United States Patent
Eisenbach-Schwartz et al.

(10) Patent No.: US 7,407,936 B2
(45) Date of Patent: *Aug. 5, 2008

(54) USE OF COPOLYMER 1 AND RELATED PEPTIDES AND POLYPEPTIDES AND T CELLS TREATED HEREWITH FOR NEUROPROTECTIVE GLAUCOMA THERAPY

(75) Inventors: Michal Eisenbach-Schwartz, Rehovot (IL); Irun R Cohen, Rehovot (IL); Michael Sela, Rehovot (IL); Eti Yoles, Rehovot (IL); Jonathan Kipnis, Modiin (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 386 days.

This patent is subject to a terminal disclaimer.

(21) Appl. No.: 11/034,262

(22) Filed: Jan. 13, 2005

(65) Prior Publication Data

US 2005/0159336 A1 Jul. 21, 2005

Related U.S. Application Data

(63) Continuation of application No. 09/765,644, filed on Jan. 22, 2001, now Pat. No. 6,844,314, which is a continuation-in-part of application No. 09/620,216, filed on Jul. 20, 2000, now abandoned, which is a continuation-in-part of application No. 09/487,793, filed on Jan. 20, 2000, now abandoned.

(60) Provisional application No. 60/209,799, filed on Jun. 7, 2000.

(51) Int. Cl.
A01N 37/18 (2006.01)

(52) U.S. Cl. .......................... 514/12; 514/18; 530/300; 424/85.1; 424/184.1; 424/185.1

(58) Field of Classification Search ........................ None
See application file for complete search history.

(56) References Cited

U.S. PATENT DOCUMENTS

| | | |
|---|---|---|
| 3,849,550 A | 11/1974 | Teitelbaum et al. |
| 6,214,791 B1 | 4/2001 | Arnon et al. |
| 6,342,476 B1 | 1/2002 | Konfino et al. |
| 6,844,314 B2 * | 1/2005 | Eisenbach-Schwartz et al. ............................ 514/2 |

FOREIGN PATENT DOCUMENTS

WO    WO 99/41247    8/1999

OTHER PUBLICATIONS

Fridkis-Hareli et al. Binding of random copolymers of three amino acids to class II MHC molecules. Int Immunol 11(5):635-641.*
Frielander, R.M. Apoptosis and Caspases in neurodegenaerative diseases. N Engl J Med 348: 1365-1375, 2000.*
Vadja, F.J.E. Neuroprotection and neurodegenerative disease. J Clin Neurosci 9: 4-8, 2002.*
Bakalash et al. Antigenic specificity of immunoprotective therapeutic vaccination for glaucoma. Invest Opthalmol Vis Sci 44(8): 3374-3381, 2003.*
Angelov et al. Therapeutic vaccine for acute and chronic motor neuron diseases: implications for amyotrophic lateral sclerosis. Proc Natl Acad Sci USA 100: 4790-4795, 2003.*
Kipnis et al. Therapeutic vaccination for closed head injury. J Neurotrauma 20(6): 559-569, 2003.*
Bakalash et al. T-cell-based vaccination for morphological and functional neuroprotection in a rat model of chronically elevated intraocular pressure. J Mol Med 83(11): 904-916, 2005.*
Schwartz et al. Protective autoimmunity and neuroprotection in inflammatory and noninflammatory neurodegenerative diseases. J Neurolog Sci 233: 163-166, 2005.*
Aharoni et al, "Copolymer 1 induces T cells of the T helper type 2 that crossreact with myelin basic protein and suppress experimental autoimmune encephalomyelitis", *Proc Natl Acad Sci USA* 94:10821-10826 (1997).
Aharoni et al "Cop-1 specific suppressor cells inhibit experimental allergic encephalomyelitis induced by either mouse spinal cord homogenate or proteolipid protein peptide 139-151", *Neurology, Meeting Info.: 49th Ann. Meeting of the American Academy of Neurology*, 48(3 (suppl. 2)):A422 (1997) (abstract).
Arnon et al, "New insights into the mechanism of action of copolymer 1 in experimental allergic encephalomyelitis and multiple sclerosis", *J Neurol* 243(4 Suppl 1):S8-13 (1996).
Bradbury et al, "NT-3, but not BDNF, prevents atrophy and death of axotomized spinal cord projection neurons", *Eur J Neurosci* 10(10):3058-3068 (1998 ).
Edwards et al, "Peptides as drugs", *QJ Med*, 92(1):1-4 (1999).
Fiegen et al, "Recent advances in Huntington's disease: implications for experimental therapeutics", *Curr Opin Neurol* 15(4):483-489 (2002).
George et al, "Axotomy-induced axonal degeneration is mediated by calcium influx through ion-specific channels", *J Neurosci* 15(10):6445-6452 (1995).
Halliday et al, "Alzheimer's disease and inflammation: a review of cellular and therapeutic mechanisms", *Clin Exp Pharmacol Physiol* 27(1-2):1-8 (2000).
Jackowski A, "Neural injury repair: hope for the future as barriers to effective CNS regeneration become clearer", *Br J Neurosurg* 9(3):303-317 (1995).

(Continued)

Primary Examiner—Marianne P Allen
(74) Attorney, Agent, or Firm—Browdy and Neimark

(57) ABSTRACT

Methods are provided for treating injury to or disease of the central or peripheral nervous system. In one embodiment, treatment is effected by administering activated T cells that recognize an antigen of Cop 1 or a Cop 1-related peptide or polypeptide to promote nerve regeneration or to prevent or inhibit neuronal degeneration within the nervous system. In another embodiment, treatment involves administering Cop 1 or a Cop 1-related peptide or polypeptide to promote nerve regeneration or to prevent or inhibit neuronal degeneration in the nervous system, either the central nervous system or the peripheral nervous system. The activated T cells, which have been activated by the presence of Cop 1 or a Cop 1-related peptide or polypeptide, can be administered alone or in combination with Cop 1 or a Cop 1-related peptide or polypeptide.

27 Claims, 10 Drawing Sheets

OTHER PUBLICATIONS

Kipnis et al, "T cell immunity to copolymer 1 confers neuroprotection on the damaged optic nerve: possible therapy for optic neuropathies", *Proc Natl Acad Sci USA*, 97:7446-7451 (2000).

Kipnis et al, "Dual action of glatiramer acetate (Cop-1) in the treatment of CNS autoimmune and neurodegenerative disorders", *Trends Mol Med* 8(7):319-323 (2002).

Miller et al, "Treatment of multiple sclerosis with copolymer-1 (Copaxone): implicating mechanisms of Th1 to Th2/Th3 immune-deviation", *J Neuroimmunol* 92(1-2):113-121 (1998).

Pan et al, "Tumor necrosis factor-alpha: a neuromodulator in the CNS", *Neurosci Biobehav Rev* 21(5):603-613 (1997).

Petrovich et al, "Pentoxifylline suppression of TNF-alpha mediated axonal degeneration in the rabbit optic nerve", *Neurol Res* 19(5):551-554 (1997).

Plata-Salaman CR, "Epidermal growth factor and the nervous system", *Peptides* 12(3):653-663 (1991).

Schori et al, "Vaccination for protection of retinal ganglion cells against death from glutamate cytotoxicity and ocular hypertension: implications for glaucoma", *Proc Natl Acad Sci USA* 98(6):3398-3403 (2001).

Schwartz M, *Drug Develop Res* 50(3-4):223-225 (2000).

Steece-Collier et al, "Etiology of Parkinson's disease: Genetics and environment revisited", *Proc Natl Acad Sci USA* 99(22):13972-13974 (2002).

Teitelbaum et al, "Copolymer 1: from basic research to clinical application", *Cell Mol Life Sci* 53(1):24-28 (1997).

Teitelbaum et al, "Immunomodulation of experimental autoimmune encephalomyelitis by oral administration of copolymer 1", *Proc Natl Acad Sci USA* 96(7):3842-3847 (1999).

Teva/Yeda/Hoechst Marion Roussel, "Copolymer-1, Glatriamer Acetate, Copaxone®: Agent for Multiple Sclerosis", *Drugs for the Future* 23(2) (1998).

\* cited by examiner

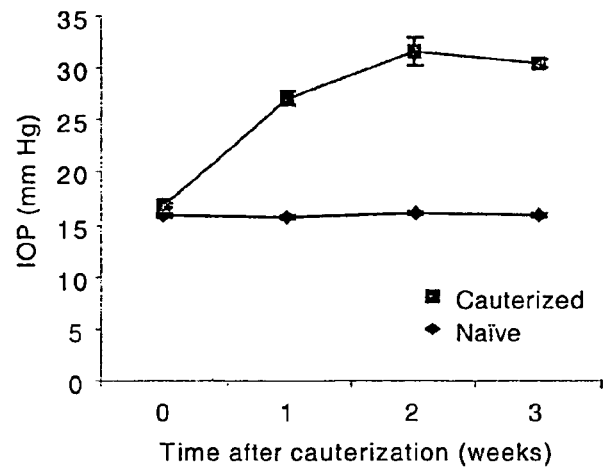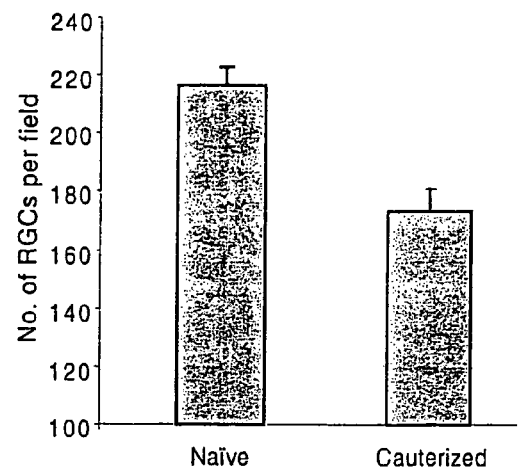
FIGURE 11A  FIGURE 11B
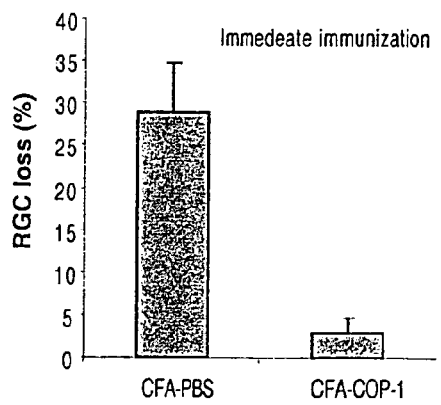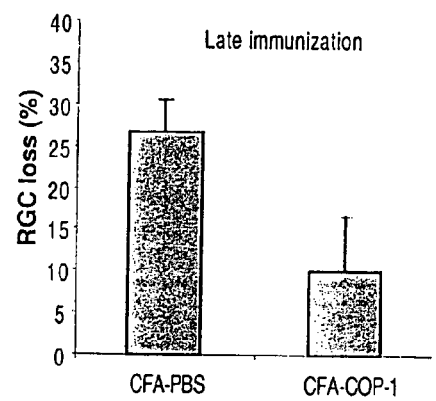
FIGURE 11C  FIGURE 11D

SEQUENCE LISTING

<160> NUMBER OF SEQ ID NOS: 33

<210> SEQ ID NO 1
<211> LENGTH: 15

-continued

```
<212> TYPE: PRT
<213> ORGANISM: Artificial Sequence
<220> FEATURE:
<223> OTHER INFORMATION: Synthetic construct

<400> SEQUENCE: 1

Ala Ala Ala Tyr Ala Ala Ala Ala Ala Ala Lys Ala Ala Ala Ala
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic construct

<400> SEQUENCE: 2

Ala Glu Lys Tyr Ala Ala Ala Ala Ala Ala Lys Ala Ala Ala Ala
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic construct

<400> SEQUENCE: 3

Ala Lys Glu Tyr Ala Ala Ala Ala Ala Ala Lys Ala Ala Ala Ala
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic construct

<400> SEQUENCE: 4

Ala Lys Lys Tyr Ala Ala Ala Ala Ala Ala Lys Ala Ala Ala Ala
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic construct

<400> SEQUENCE: 5

Ala Glu Ala Tyr Ala Ala Ala Ala Ala Ala Lys Ala Ala Ala Ala
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic construct

<400> SEQUENCE: 6

Lys Glu Ala Tyr Ala Ala Ala Ala Ala Ala Lys Ala Ala Ala Ala
1               5                   10                  15

<210> SEQ ID NO 7
<211> LENGTH: 15
<212> TYPE: PRT
```

```
<213> ORGANISM: Artificial Sequence
<220> FEATURE:
<223> OTHER INFORMATION: Synthetic construct

<400> SEQUENCE: 7

Ala Glu Glu Tyr Ala Ala Ala Ala Ala Lys Ala Ala Ala Ala
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic construct

<400> SEQUENCE: 8

Ala Ala Glu Tyr Ala Ala Ala Ala Ala Lys Ala Ala Ala Ala
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic construct

<400> SEQUENCE: 9

Glu Lys Ala Tyr Ala Ala Ala Ala Ala Lys Ala Ala Ala Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic construct

<400> SEQUENCE: 10

Ala Ala Lys Tyr Glu Ala Ala Ala Ala Lys Ala Ala Ala Ala
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic construct

<400> SEQUENCE: 11

Ala Ala Lys Tyr Ala Glu Ala Ala Ala Lys Ala Ala Ala Ala
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic construct

<400> SEQUENCE: 12

Glu Ala Ala Tyr Ala Ala Ala Ala Ala Lys Ala Ala Ala Ala
1               5                   10                  15

<210> SEQ ID NO 13
<211> LENGTH: 15
<212> TYPE: PRT
<213> ORGANISM: Artificial Sequence
```

```
<220> FEATURE:
<223> OTHER INFORMATION: Synthetic construct

<400> SEQUENCE: 13

Glu Lys Lys Tyr Ala Ala Ala Ala Ala Lys Ala Ala Ala Ala
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic construct

<400> SEQUENCE: 14

Glu Ala Lys Tyr Ala Ala Ala Ala Ala Lys Ala Ala Ala Ala
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic construct

<400> SEQUENCE: 15

Ala Glu Lys Tyr Ala Ala Ala Ala Ala Ala Ala Ala Ala Ala
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic construct

<400> SEQUENCE: 16

Ala Lys Glu Tyr Ala Ala Ala Ala Ala Ala Ala Ala Ala Ala
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic construct

<400> SEQUENCE: 17

Ala Lys Lys Tyr Glu Ala Ala Ala Ala Ala Ala Ala Ala Ala
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic construct

<400> SEQUENCE: 18

Ala Lys Lys Tyr Ala Glu Ala Ala Ala Ala Ala Ala Ala Ala
1               5                   10                  15

<210> SEQ ID NO 19
<211> LENGTH: 15
<212> TYPE: PRT
<213> ORGANISM: Artificial Sequence
<220> FEATURE:
```

<223> OTHER INFORMATION: Synthetic construct

<400> SEQUENCE: 19

Ala Glu Ala Tyr Lys Ala Ala Ala Ala Ala Ala Ala Ala Ala Ala
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic construct

<400> SEQUENCE: 20

Lys Glu Ala Tyr Ala Ala Ala Ala Ala Ala Ala Ala Ala Ala Ala
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic construct

<400> SEQUENCE: 21

Ala Glu Glu Tyr Lys Ala Ala Ala Ala Ala Ala Ala Ala Ala Ala
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic construct

<400> SEQUENCE: 22

Ala Ala Glu Tyr Lys Ala Ala Ala Ala Ala Ala Ala Ala Ala Ala
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic construct

<400> SEQUENCE: 23

Glu Lys Ala Tyr Ala Ala Ala Ala Ala Ala Ala Ala Ala Ala Ala
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic construct

<400> SEQUENCE: 24

Ala Ala Lys Tyr Glu Ala Ala Ala Ala Ala Ala Ala Ala Ala Ala
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic construct

<400> SEQUENCE: 25

Ala Ala Lys Tyr Ala Glu Ala Ala Ala Ala Ala Ala Ala Ala Ala
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthetic construct

<400> SEQUENCE: 26

Glu Lys Lys Tyr Ala Ala Ala Ala Ala Ala Ala Ala Ala Ala Ala
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic construct

<400> SEQUENCE: 27

Glu Ala Lys Tyr Ala Ala Ala Ala Ala Ala Ala Ala Ala Ala Ala
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic construct

<400> SEQUENCE: 28

Ala Glu Tyr Ala Lys Ala Ala Ala Ala Ala Ala Ala Ala Ala Ala
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic construct

<400> SEQUENCE: 29

Ala Glu Lys Ala Tyr Ala Ala Ala Ala Ala Ala Ala Ala Ala Ala
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic construct

<400> SEQUENCE: 30

Glu Lys Tyr Ala Ala Ala Ala Ala Ala Ala Ala Ala Ala Ala Ala
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic construct

```
-continued

<400> SEQUENCE: 31

Ala Tyr Lys Ala Glu Ala Ala Ala Ala Ala Ala Ala Ala Ala Ala
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic construct

<400> SEQUENCE: 32

Ala Lys Tyr Ala Glu Ala Ala Ala Ala Ala Ala Ala Ala Ala Ala
1               5                   10                  15

<210> SEQ ID NO 33
<211> LENGTH: 22
<212> TYPE: PRT
<213> ORGANISM: Homo sapiens

<400> SEQUENCE: 33

Gly Gln Phe Arg Val Ile Gly Pro Gly His Pro Ile Arg Ala Leu Val
1               5                   10                  15

Gly Asp Glu Ala Glu Leu
            20
```

US 7,407,936 B2

USE OF COPOLYMER 1 AND RELATED PEPTIDES AND POLYPEPTIDES AND T CELLS TREATED HEREWITH FOR NEUROPROTECTIVE GLAUCOMA THERAPY

FIELD OF THE INVENTION

The present invention relates to compositions and methods for the promotion of nerve regeneration or prevention or inhibition of neuronal degeneration to ameliorate the effects of injury or disease of the nervous system (NS). In particular, the invention relates to compositions comprising Copolymer 1 (Cop 1) or a Cop 1-related peptide or polypeptide, and/or activated T cells treated with Cop 1 or a Cop 1-related peptide or polypeptide, to promote nerve regeneration or to prevent or inhibit neuronal degeneration caused by injury or disease of nerves within the central nervous system or peripheral nervous system of a human subject. The compositions of the present invention may be administered alone or may be optionally administered in any desired combination.

BACKGROUND OF THE INVENTION

The nervous system comprises the central and the peripheral nervous system. The central nervous system (CNS) is composed of the brain and spinal cord; the peripheral nervous system (PNS) consists of all of the other neural elements, namely the nerves and ganglia outside of the brain and spinal cord.

Damage to the nervous system may result from a traumatic injury, such as penetrating trauma or blunt trauma, or a disease or disorder, including but not limited to Alzheimer's disease, Parkinson's disease, Huntington's disease, amyotrophic lateral sclerosis (ALS), diabetic neuropathy, senile dementia, and ischemia.

Maintenance of central nervous system integrity is a complex "balancing act" in which compromises are struck with the immune system. In most tissues, the immune system plays an essential part in protection, repair, and healing. In the central nervous system, because of its unique immune privilege, immunological reactions are relatively limited (Streilein, 1993, 1995). A growing body of evidence indicates that the failure of the mammalian central nervous system to achieve functional recovery after injury is a reflection of an ineffective dialog between the damaged tissue and the immune system. For example, the restricted communication between the central nervous system and blood-borne macrophages affects the capacity of axotomized axons to regrow; transplants of activated macrophages can promote central nervous system regrowth (Lazarov-Spiegler et al, 1996; Rapalino et al, 1998).

Activated T cells have been shown to enter the central nervous system parenchyma, irrespective of their antigen specificity, but only T cells capable of reacting with a central nervous system antigen seem to persist there (Hickey et al, 1991; Werkele, 1993; Kramer et al, 1995). T cells reactive to antigens of central nervous system white matter, such as myelin basic protein (MBP), can induce the paralytic disease experimental autoimmune encephalomyelitis (EAE) within several days of their inoculation into naive recipient rats (Ben-Nun, 1981a). Anti-MBP T cells may also be involved in the human disease multiple sclerosis (Ota, K. et al, 1990; Martin, 1997). However, despite their pathogenic potential, anti-MBP T cell clones are present in the immune systems of healthy subjects (Burns, 1983; Pette, M. et al, 1990; Martin et al, 1990; Schluesener et al, 1985). Activated T cells, which normally patrol the intact central nervous system, transiently accumulate at sites of central nervous system white matter lesions (Hirschberg et al, 1998).

A catastrophic consequence of central nervous system injury is that the primary damage is often compounded by the gradual secondary loss of adjacent neurons that apparently were undamaged, or only marginally damaged, by the initial injury (Faden et al, 1992; Faden 1993; McIntosh, 1993). The primary lesion causes changes in extracellular ion concentrations, elevation of amounts of free radicals, release of neurotransmitters, depletion of growth factors, and local inflammation. These changes trigger a cascade of destructive events in the adjacent neurons that initially escaped the primary injury (Lynch et al, 1994; Bazan et al, 1995; Wu et al, 1994). This secondary damage is mediated by activation of voltage-dependent or agonist-gated channels, ion leaks, activation of calcium-dependent enzymes such as proteases, lipases and nucleases, mitochondrial dysfunction and energy depletion, culminating in neuronal cell death (Yoshino et al, 1991; Hovda et al, 1991; Zivin et al, 1991; Yoles et al, 1992). The widespread loss of neurons beyond the loss caused directly by the primary injury has been called "secondary degeneration."

One of the most common mediators which cause self-propagation of the diseases even when the primary risk factor is removed or attenuated is glutamate, an excitatory amino acid capable of displaying dual activity: playing a pivotal role in normal central nervous system (CNS) functioning as an essential neurotransmitter, but becoming toxic when its physiological levels are exceeded. Elevation of glutamate has been reported in many CNS disorders. In its role as an excitotoxic compound, glutamate is one of the most common mediators of toxicity in acute and chronic (including optic nerve degeneration in glaucoma) degenerative disorders (Pitt et al, 2000 and Schoepp et al, 1996). Endogenous glutamate has been attributed to the brain damage occurring acutely after status epilepticus, cerebral ischemia or traumatic brain injury. It may also contribute to chronic neurodegeneration in such disorders as amyotrophic lateral sclerosis and Huntington's chorea.

Intensive research has been devoted to attenuating the cytotoxic effect of glutamate by the use of locally acting drugs, such as NMDA-receptor antagonists (Brauner-Osborne et al, 2000). Conventional therapy of this type is often unsatisfactory, however, as in neutralizing the toxic effect it is likely to interfere with the physiological functioning. In humans, such compounds have psychotropic and other side effects that make them unsuitable as therapeutic agents. They also have the disadvantage of interfering with the essential physiological functioning of glutamate as a ubiquitous CNS neurotransmitter. Because glutamate activity is essential for normal physiological functioning, yet is potentially devastating after acute injury or in chronic CNS disorders, any attempt to neutralize its harmful effect must do so without eliminating its essential activity at other sites in the body.

Another tragic consequence of central nervous system injury is that neurons in the mammalian central nervous system do not undergo spontaneous regeneration following an injury. Thus, a central nervous system injury causes permanent impairment of motor and sensory functions.

Spinal cord lesions, regardless of the severity of the injury, initially result in a complete functional paralysis known as spinal shock. Some spontaneous recovery from spinal shock may be observed, starting a few days after the injury and tapering off within three to four weeks. The less severe the insult, the better the functional outcome. The extent of recovery is a function of the amount of undamaged tissue minus the loss due to secondary degeneration. Recovery from injury would be improved by neuroprotective treatment that could reduce secondary degeneration. For example, alleviation of the effect of glutamate is a frequent target of neuroprotective drug development. Among the drugs which are being developed for this purpose are N-methyl-D-aspartate (NMDA)-receptor or alpha-amino-3-hydroxy-5-methyl-4-isoxazoleproprionic acid (AMPA)-receptor antagonists. These drugs will inevitably have severe side effects as they interfere with the functioning of NMDA and AMPA receptors, which are crucial for CNS activity. One of the most intensely studied NMDA-receptor antagonists is MK801, which provides effective neuroprotection but with severe side effects. In animal models of cerebral ischemia and traumatic brain injury, NMDA and AMPA receptor antagonists protect against acute brain damage and delayed behavioral deficits. Such compounds are undergoing testing in humans, but therapeutic efficacy has yet to be established. Other clinical conditions that may respond to drugs acting on glutamatergic transmission include epilepsy, amnesia, anxiety, hyperalgesia and psychosis (Meldrum, 2000).

In the laboratory of the present inventors, it has recently been discovered that activated T cells that recognize an antigen of the nervous system (NS) of the patient promote nerve regeneration or confer neuroprotection. Reference is made to PCT publication WO 99/60021, the entire contents of which is hereby incorporated herein by reference. More specifically, T cells reactive to MBP were shown to be neuroprotective in rat models of partially crushed optic nerve (Moalem et al, 1999) and of spinal cord injury (Hauben et al, 2000). Until recently, it had been thought that the immune system excluded immune cells from participating in nervous system repair. It was quite surprising to discover that NS-specific activated T cells could be used to promote nerve regeneration or to protect nervous system tissue from secondary degeneration which may follow damage caused by injury or disease of the CNS or PNS.

NS-specific activated T cells as described in said WO 99/60021 publication are activated T cells having specificity for an antigen of the NS of a patient. The antigen used to confer the specificity to the T cells may be a self NS-antigen of the patient, a peptide derived therefrom, or an NS-antigen of another individual or even another species, or a peptide derived therefrom, as long as the activated T cell recognizes an antigen in the NS of the patient.

Said NS-specific activated T cells are for use to promote nerve regeneration or to prevent or inhibit the effects of disease. If the disease being treated is an autoimmune disease, in which the autoimmune antigen is an NS antigen, the T cells which are used for the treatment of neural damage or degeneration caused by such disease are not activated against the same autoimmune antigen involved in the disease.

The above-referenced PCT publication WO 99/60021 discloses that therapy for amelioration of effects of injury or disease comprising administration of NS-specific activated T cells may optionally be in combination with an NS-specific antigen or peptide derived therefrom. An NS-specific antigen as defined in said WO 99/60021 refers to an antigen that specifically activates T cells such that following activation, the activated T cells accumulate at a site of injury or disease in the NS of the patient. Furthermore, oral administration of NS-specific antigen or a peptide derived therefrom can be combined with active immunization to build up a critical T cell response immediately after injury.

In this prior invention, the NS-specific antigen used to activate the T cells in vitro or in vivo or to immunize the patient, may be an antigen obtained from NS tissue, preferably from tissue at a site of CNS injury or disease. Natural or synthetic NS-specific antigens or epitopes were disclosed to include MBP, MOG, PLP, MAG, S-100, β-amyloid, Thy-1, P0, P2 and a neurotransmitter receptor. Specific illustrative examples of such useful NS-specific antigens disclosed in WO 99/60021 are human MBP, human proteolipid protein (PLP), and human oligodendrocyte glycoprotein. Also disclosed were peptides derived from NS-specific, self-antigens or derivatives of NS-specific antigens that activate T cells, but do not induce an autoimmune disease, such as a peptide comprising amino acids 51-70 of myelin basic protein (MBP).

The mechanism of action of such NS-specific T cells has yet to be discovered, but the massive accumulation of exogenously administered T cells at the site of CNS injury suggests that the presence of T cells at the site of injury plays a prominent role in neuroprotection. It appears, however, that the accumulation, though a necessary condition, is not sufficient for the purpose, as T cells specific to the non-self antigen ovalbumin also accumulate at the site, but have no neuroprotective effect (Hirschberg et al, 1998).

A high molecular weight synthetic basic random copolymer consisting of L-Ala, L-Glu, L-Lys and L-Tyr residues in the molar ratio of about 6 parts Ala to 2 parts Glu to 4.5 parts Lys to 1 part Tyr, and having a molecular weight of 15,000-25,000, was first described in U.S. Pat. No. 3,849,550 as an agent for treatment or prevention of experimental allergic encephalomyelitis (EAE), a disease resembling multiple sclerosis (MS) that can be induced in susceptible animals. Batches of this copolymer of average molecular weight 23,000, designated Copolymer 1 or Cop 1, were shown to be highly effective in protecting and suppressing EAE in several animal species (Teitelbaum et al, 1971, 1974a, 1974b).

Later, Cop 1 was found to significantly reduce the number of relapses in patients with the exacerbating-remitting form of MS (Bornstein et al, 1990; Sela et al, 1990; Johnson et al, 1994). Copolymer 1, in the form of the acetate salts of synthetic polypeptides containing L-Glu, L-Ala, L-Tyr and L-Lys with an average molar fraction of 0.141, 0.427, 0.095 and 0.338, is the active ingredient of COPAXONE®, a medicament for the treatment of multiple sclerosis.

It is thus apparent that the effect of Copolymer 1 in the treatment of MS is in in the achievement of suppression or deactivation of autoimmune T cell reactivity to myelin antigens in multiple sclerosis patients. For this purpose, Copolymer 1 is administered without adjuvants by daily subcutaneous injection.

Cop 1 was originally designed to mimic MBP and to induce EAE, but was found to be non-encephalitogenic and even to suppress EAE induced by MBP (Teitelbaum et al, 1971) (PLP) (Teitelbaum et al, 1996), or (MOG) (Ben-Nun et al, 1996). The precise mechanisms by which Cop 1 prevents the development of EAE and ameliorates multiple sclerosis (MS) are not yet known. Nevertheless, some important immunological properties of this copolymer have emerged. Studies have demonstrated partial cross-reactivity of Cop 1 with MBP at both the T cell (Webb et al, 1973) and the antibody (Teitelbaum et al, 1988) level. Cop 1 can serve as an antagonist of the T-cell antigen receptor for the MBP immunodominant epitope (Aharoni, 1998). It can also bind to various MHC class II molecules and prevent them from binding to T cells with specific antigen-recognition properties (Fridkis-Hareli et al, 1999a). In rodents, Cop 1 induces regulatory cells that probably act as bystander suppressors (Aharoni, 1998) of encephalitogenic T cells. Adoptive transfer of such T cells was found to prevent the development of EAE induced by MBP (Aharoni et al, 1993), PLP (Aharoni, 1998), or whole spinal cord homogenate (Aharoni et al, 1997).

Furthermore, direct evidence has also been reported both for competitive interaction of Cop 1 and related copolymers and Collagen II (CII) peptide with rheumatoid arthritis (RA)-associated HLA-DR molecules and for inhibition of CII-specific T cell responses, suggesting that these compounds may be effective against rheumatoid arthritis (Fridkis-Hareli, 1998, 1999b).

Oral administration of autoantigen in order to obtain "oral tolerance" has been disclosed for the treatment of various autoimmune diseases. For example, EP 359 783 discloses the oral administration of MBP for the treatment of multiple sclerosis. PCT International Publications WO 91/12816, WO 91/08760 and WO 92/06704 all disclose the treatment of other autoimmune diseases using the oral tolerance method with a variety of autoantigens. Treatment of multiple sclerosis by ingestion or inhalation of Copolymer 1, to achieve suppression of the autoimmune T cell response to myelin antigens, has been disclosed in PCT publication WO 98/30227.

Compounds related to Copolymer 1 have also been studied and found to have properties similar to Copolymer 1. For example, copolymers composed of three of the four amino acids found in Copolymer 1 bind to purified Class II MHC molecules (Fridkis-Hareli et al, 1999a, WO 005250). In addition, binding motifs of Copolymer 1 to multiple sclerosis- and rheumatoid arthritis-associated HLA-DR molecules have recently been elucidated (Fridkis-Hareli et al, 1999b). From these binding motifs, polypeptides of fixed sequence can readily be proposed and tested for binding to the peptide binding groove of the HLA-DR molecules. Such peptides would be expected to act in a way similar to Cop 1 itself. Examples of such synthetic peptides are disclosed in WO 005249.

Citation or identification of any reference in this section or any other part of this application shall not be construed as an admission that such reference is available as prior art to the invention.

SUMMARY OF THE INVENTION

The present invention is directed to methods and compositions for the promotion of nerve regeneration or prevention or inhibition of neuronal degeneration to ameliorate and treat the effects of injury to, or disease of, the nervous system (NS). The present invention is based in part on the applicants' unexpected discovery that activated T cells against Cop 1 promote nerve regeneration or confer neuroprotection. It is further based in part on the present inventors' unexpected discovery that activated T cells against Cop 1 protect nerve cells from glutamate toxicity. As used herein, "neuroprotection" refers to the prevention or inhibition of degenerative effects of injury or disease in the NS, including protection from the secondary neurodegenerative effects which persist even when the primary risk factor is removed or attenuated. This includes protection of both white matter and gray matter. Until recently, it was thought that the immune system excluded immune cells from participating in nervous system repair. It was quite surprising to discover that Cop 1 activated T cells can be used to promote nerve regeneration or to protect nervous system tissue from secondary degeneration which may follow damage caused by injury or disease of the CNS or PNS.

"Activated T cell" as used herein includes (i) T cells that have been activated by exposure to Cop 1 or a.

Cop 1-related peptide or polypeptide and (ii) progeny of such activated T cells.

In one embodiment, the present invention provides pharmaceutical compositions comprising a therapeutically effective amount of Cop 1-specific activated T cells and methods for using such compositions to promote nerve regeneration or to prevent or inhibit neuronal degeneration in the CNS or PNS, in an amount which is effective to ameliorate the effects of an injury or disease of the NS. "Cop 1-specific activated T cells" as used herein refers to activated T cells having specificity for Cop 1 or a Cop 1-related peptide or polypeptide.

The Cop 1-specific activated T cells are used to promote nerve regeneration or to prevent or inhibit the secondary degenerative effects which may follow primary NS injury or the effects of neurodegenerative processes caused by a disease or condition as described in Section (3) hereinafter, but excluding multiple sclerosis. Non-limiting examples include glaucoma, stroke, ischemia, gunshot, and cerebral damage caused by dangerous sports. The Cop 1-specific activated T cells serve not only to provide neuroprotection against primary and secondary risk factors associated with myelin (white matter) but also against primary and secondary risk factors associated with the neuronal cell bodies themselves (gray matter) in view of the discovered protection against glutamate toxicity. Thus Cop 1-specific activated T cells, are expected to be useful for the purpose of the present invention and would not have been suggested by known immunotherapy techniques.

Furthermore, as Cop 1 protects from glutamate toxicity, its action is not solely via cross-reactivity with myelin. It must also have a regulatory activity, such as by creating regulatory cells or regulatory substances. In view of this regulatory activity, the Cop 1 vaccination and the Cop-1 specific activated T cells are expected also to protect white matter and gray matter from damage caused by oxidative stress and other sources of damage to neural cells. In addition, because of this regulatory activity, the present invention can also be used to protect neural cells not only from multiple sclerosis, as has been suggested in the prior art, but also from autoimmune diseases other than multiple sclerosis.

The present invention also provides pharmaceutical compositions comprising a therapeutically effective amount of Cop 1 or a Cop 1-related peptide or polypeptide and methods of use of such compositions to promote nerve regeneration or to prevent or inhibit neuronal degeneration in the CNS or PNS, in which the amount is effective to activate T cells in vivo or in vitro, wherein the activated T cells inhibit or ameliorate the effects of an injury or disease of the NS.

In the practice of the invention, therapy for amelioration and treatment of effects of injury or disease comprising administration of Cop 1-specific activated T cells may optionally be in combination with Cop 1 or a Cop 1-related peptide or polypeptide.

Additionally, oral administration of Cop 1 or a Cop 1-related peptide or polypeptide antigen is effective for neuroprotection after priming with Cop 1 administered in adjuvant. Thus, oral Cop 1 can be used to boost the activity of the T cells, subsequent to primary activation of such Cop 1, preferably in adjuvant, to build up a critical T cell response immediately after injury.

In another embodiment, cell banks can be established to store Cop 1 sensitized T cells for neuroprotective treatment of individuals at a later time, as needed. In this case, autologous T cells may be obtained from an individual. Alternatively, allogeneic or semi-allogeneic T cells may be stored such that a bank of T cells of each of the most common MHC-class II types are present. In case an individual is to be treated for an injury, preferably autologous stored T cells are used, but, if autologous T cells are not available, then cells should be used which share an MHC type II molecule with the patient, and these would be expected to be operable in that individual. The cells are preferably stored in an activated state after exposure to Cop 1 or a Cop 1-related peptide or polypeptide. However, the cells may also be stored in a resting state and activated once they are thawed and prepared for use. The cell lines of the bank are preferably cryopreserved. The cell lines are prepared in any way which is well known in the art. Once the cells are thawed, they are preferably cultured prior to injection in order to eliminate non-viable cells. During this culturing, the cells can be activated or reactivated using the Cop 1 antigen or peptide as used in the original activation. Alternatively, activation may be achieved by culturing in the presence of a mitogen, such as phytohemagglutinin (PHA) or concanavalin A (preferably the former). This will place the cells into an even higher state of activation. The few days that it takes to culture the cells should not be detrimental to the patient as the treatment in accordance with the present invention may occur any time up to a week or more after the injury in order to still be effective. Alternatively, if time is of the essence, the stored cells may be administered immediately after thawing.

BRIEF DESCRIPTION OF THE DRAWINGS

In FIG. 5A, C57BL/6J mice were immunized with pMOG 14 days before their RGCs were exposed directly to glutamate toxicity by intravitreous injection of L-glutamate (200 nmole). Four days later, the RGCs were retrogradely labeled with FluoroGold, and this was followed after 3 days by retinal excision and counting (see Material and Methods section of Example 3, Experiment 2). RGC survival is expressed as the mean±SEM per mm$^2$. No significant differences in RGC survival after glutamate injection were observed between the group treated with pMOG in CFA (n=8) and the control group treated with PBS in CFA (n=7). In FIG. 5B, glutamate was injected intravitreally into Lewis rats. Four days later, the RGCs were labeled by application of the dye 4-Di-10-Asp, and this was followed after 5 days by retinal excision and counting. Note that retinal survival in the T-cell-treated group did not differ significantly from that in the control group (no. of RGCs per mm$^2$, mean±SEM (n=6 in each group))

In FIG. 8A, ten days before glutamate injection, mice were immunized by subcutaneous injection with Cop-1 in CFA (5 mg/ml bacteria) or injected with PBS in CFA. The results of one experiment are shown (n=5 in each group). The number of surviving RGCs per mm$^2$ (mean±SEM) was significantly higher in the Cop-1-immunized mice than in the mice injected with PBS in CFA or in mice that received glutamate only ($p<0.02$, 2-tailed t-test). Injection with PBS in CFA had no detectable effect on the number of RGCs. The experiment was repeated three times, with identical results. Altogether 13 animals in the Cop-1 treated group and 15 animals in the PBS-treated group were tested. In FIG. 8B, immediately after intravitreal injection of glutamate, mice were immunized with Cop-1 emulsified in CFA (5 mg/ml bacteria). The number of surviving RGCs per mm$^2$ (mean±SEM) was determined 1 week later. The results of one experiment are shown. The effect of immunization with Cop-1 was significant ($p<0.05$; 2-tailed t-test; n=12 for Cop-1 and n=8 for the control). This experiment was repeated using 11 mice for Cop-1 immunization and 8 mice for injection with PBS in CFA (5 mg/ml bacteria). In FIG. 8C, RGCs survival following glutamate insult and immediate immunization with Cop-1 in adjuvant containing 0.5 mg/ml of bacteria. The number of surviving RGCs per mm$^2$ was significantly higher in the Cop-1-immunized mice (n=15) than in the mice injected with glutamate (n=5) (p<0.04; 2-tailed t-test). In FIG. 8D, Survival of RGCs after immunization performed before, immediately after, or 48 h after glutamate insult. Bars show the pooled results obtained for all mice examined in each treatment, collected from repeated experiments. No effect was seen when immunization was performed 48 h after the insult

FIGS. 11A-11D show the effect of chronically increased IOP and Cop-1 immunization on retinal ganglion cell survival in Lewis rats. In FIG. 11A, laser cauterization causing occlusion of the episcleral and limba1 veins results in an increase in IOP and subsequent death of retinal ganglion cells. Three weeks after lasering, the mean IOP was 30.4±0.42 mm Hg (mean±SEM, n=5) in rats subjected to venous occlusion compared to 15.8±0.2 mm Hg (n=7) in naive rats. In FIG. 11B, three weeks after venous occlusion, 19.9%±0.51% (mean±SEM) fewer retinal ganglion cells were counted in the laser-treated rats than in naïve rats. In FIG. 11C, immunization with Cop-1 immediately after venous occlusion reduces retinal ganglion cell loss. Rats were immunized with Cop-1 (200 µg) in CFA (n=15) or injected with PBS (n=13) in CFA immediately after lasering. Three weeks later, the retinas were excised and whole-mounted, and the numbers of retinal ganglion cells pre-labeled with rhodamine dextran amine were counted. Bars represent the retinal ganglion cell loss in each group of rats, calculated as a percentage of the number of retinal ganglion cells in naïve rats (mean±SEM). The difference in the numbers of retinal ganglion cells in the 2 groups was significant (p<0.0001, 2-tailed t-test). In FIG. 11D, the effect of delayed immunization with Cop-1 on retinal ganglion cell loss was examined by immunizing rats 10 days after venous occlusion. Bars represent retinal ganglion cell loss in groups treated with Cop-1 (n=5) or PBS (n=4), calculated as a percentage of the number of retinal ganglion cells (mean±SEM) in naïve animals. A tendency towards a neuroprotective effect was observed after delayed immunization with Cop-1; the difference was significant only by 1-tailed t-test (p=0.04).

DETAILED DESCRIPTION OF THE INVENTION

Figure 1A:
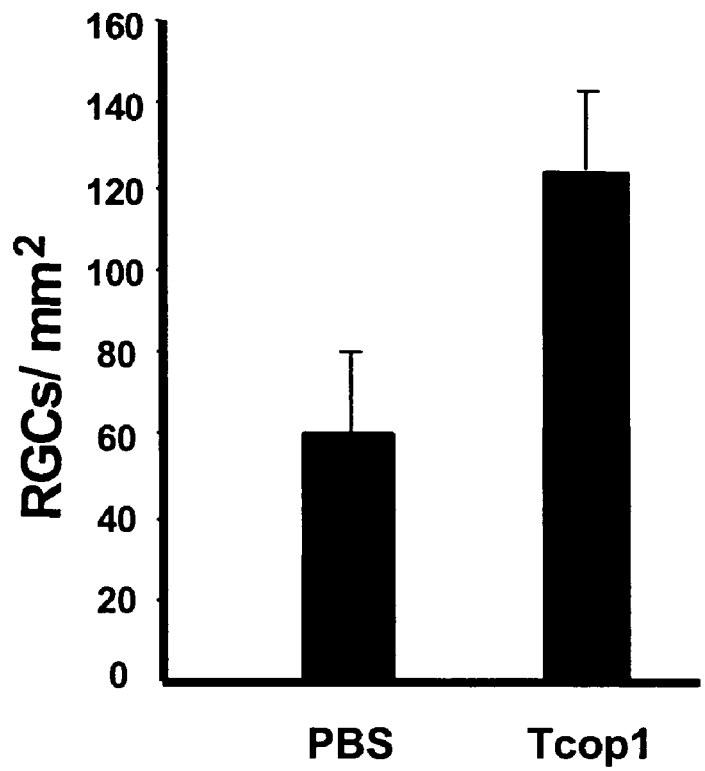
FIGS. 1A and 1B are graphs showing the number of labeled (surviving) RGCs/mm$^2$ in retinas excised from rats who had been injected with PBS in incomplete Freund's adjuvant (IFA) (labeled PBS in the figures) or with Cop 1-specific T cells in IFA (labeled Tcop1) immediately after mild (FIG. 1A) or severe (FIG. 1B) optic nerve injury.

Merely for ease of explanation, the detailed description of the present invention is divided into the following subsections: (1) Cop 1 Specific Activated T Cells; (2) Cop 1 and Cop 1-Related Peptides and Polypeptides; (3) Therapeutic Uses; (4) Formulations and Administration; (5) Establishment of Autologous Cell Banks for T Lymphocytes; (6) Examples; and (7) Discussion of Results.

(1) Cop 1 Specific Activated T Cells

Cop 1-specific activated T cells (ATCs) are T cells which have been activated in the presence of Cop 1 or a Cop 1-related peptide or polypeptide, as defined in Section (2). Such ATCs can be used for treating, i.e., ameliorating or inhibiting, the effects of injury or disease of the CNS or PNS that result in NS degeneration or for promoting regeneration in the NS, in particular the CNS. In addition, as glutamate is a mediator in all neurodegenerative diseases, whether chronic or acute, it is intended that such ATCs can be used for protecting CNS cells from glutamate toxicity and for treating diseases or conditions caused or exacerbated by glutamate toxicity, such as abnormal intraocular pressure.

The Cop 1-specific activated T cells are preferably autologous, most preferably of the CD4 and/or CD8 phenotypes, but they may also be allogeneic T cells from related donors, e.g., siblings, parents, children, or HLA-matched or partially matched, semi-allogeneic or fully allogeneic donors.

In addition to the use of autologous T cells isolated from the subject, the present invention also comprehends the use of semi-allogeneic T cells for neuroprotection. These T cells may be prepared as short- or long-term lines and stored by conventional cryopreservation methods for thawing and administration, either immediately or after culturing for 1-3 days, to a subject suffering from injury to the central nervous system and in need of T cell neuroprotection.

The use of semi-allogeneic T cells is based on the fact that T cells can recognize a specific antigen epitope presented by foreign antigen presenting cells (APC), provided that the APC express the MHC molecule, class I or class II, to which the specific responding T cell population is restricted, along with the antigen epitope recognized by the T cells. Thus, a semi-allogeneic population of T cells that can recognize at least one allelic product of the subject's MHC molecules, preferably an HLA-DR or an HLA-DQ or other HLA molecule, and that is specific for a Cop 1 epitope, will be able to recognize the antigens cross-reactive with Cop 1 in the subject's area of NS damage and produce the needed neuroprotective effect. There is little or no polymorphism in the adhesion molecules, leukocyte migration molecules, and accessory molecules needed for the T cells to migrate to the area of damage, accumulate there, and undergo activation. Thus, the semi-allogeneic T cells will be able to migrate and accumulate at the CNS site in need of neuroprotection and will be activated to produce the desired effect.

It is known that semi-allogeneic T cells will be rejected by the subject's immune system, but that rejection requires about two weeks to develop. Hence, the semi-allogeneic T cells will have the two-week window of opportunity needed to exert neuroprotection. After two weeks, the semi-allogeneic T cells will be rejected from the body of the subject, but that rejection is advantageous to the subject because it will rid the subject of the foreign T cells and prevent any untoward consequences of the activated T cells. The semi-allogeneic T cells thus provide an important safety factor and are a preferred embodiment.

It is known that a relatively small number of HLA class II molecules are shared by most individuals in a population. For example, about 50% of the Jewish population express the HLA-DR5 gene. Thus, a bank of specific T cells reactive to Cop 1 epitopes that are restricted to HLA-DR5 would be useful in 50% of that population. The entire population can be covered essentially by a small number of additional T cell lines restricted to a few other prevalent HLA molecules, such as DR1, DR4, DR2, etc. Thus, a functional bank of uniform T cell lines can be prepared and stored for immediate use in almost any individual in a given population. Such a bank of T cells would overcome any technical problems in obtaining a sufficient number of specific T cells from the subject in need of neuroprotection during the open window of treatment opportunity. The semi-allogeneic T cells will be safely rejected after accomplishing their role of neuroprotection. This aspect of the invention does not contradict, and is in addition to the use of autologous T cells as described herein.

The Cop 1-specific activated T cells are preferably non-attenuated, although attenuated Cop 1-specific activated T cells may be used. T cells may be attenuated using methods well known in the art, including but not limited to, by gamma-irradiation, e.g., 1.5-10.0 Rads (Ben-Nun et al, 1981b; Ben-Nun et al, 1982); and/or by pressure treatment, for example as described in U.S. Pat. No. 4,996,194 (Cohen et al). In a preferred embodiment the Cop 1-specific activated T cells are isolated as described below. T cells can be isolated and purified according to methods known in the art (Mor et al, 1995). For an illustrative example, see Section (6), Example 1.

Circulating T cells of a subject which recognize Cop 1 are isolated and expanded using known procedures. In order to obtain Cop 1-specific activated T cells, T cells are isolated and the Cop 1-specific ATCs are then expanded by a known procedure (Burns et al, 1983; Pette et al, 1990; Martin et al, 1990; Schluesener et al, 1985; Suruhan-Direskeneli et al, 1993, which are incorporated herein by reference in their entirety).

During ex vivo activation of the T cells, the T cells may be activated by culturing them in medium to which at least one suitable growth promoting factor has been added. Growth promoting factors suitable for this purpose include, without limitation, cytokines, for instance tumor necrosis factor α (TNF-α), interleukin 2 (IL-2), and interleukin 4 (IL-4).

In one embodiment, the activated T cells endogenously produce a substance that ameliorates the effects of injury or disease in the NS.

In another embodiment, the activated T cells endogenously produce a substance that stimulates other cells, including, but not limited to, transforming growth factor-β (TGF-β), nerve growth factor (NGF), neurotrophic factor 3 (NT-3), neurotrophic factor 4/5 (NT-4/5), brain derived neurotrophic factor (BDNF); interferon-γ (IFN-γ), and interleukin-6 (IL-6), wherein the other cells, directly or indirectly, ameliorate the effects of injury or disease.

Following their proliferation in vitro, the T cells are administered to a mammalian subject. In a preferred embodiment, the T cells are administered to a human subject. T cell expansion is preferably performed using Cop 1 or a Cop 1-related peptide or polypeptide.

Cop 1-activated T cells can be used immediately or may be preserved for later use, e.g., by cryopreservation as described below. Cop 1-specific activated T cells may also be obtained using previously cryopreserved T cells, i.e., after thawing the cells, the T cells may be incubated with Cop 1 or a Cop 1-related peptide or polypeptide, optimally together with peripheral blood lymphocytes (PBL), to obtain a preparation of Cop 1-specific ATCs.

As will be evident to those skilled in the art, the T cells can be preserved, e.g., by cryopreservation, either before or after culture.

Cryopreservation agents which can be used include but are not limited to dimethyl sulfoxide (DMSO) (Lovelock et al, 1959; Ashwood-Smith, 1961), glycerol, polyvinylpyrrolidone (Rinfret, 1960), polyethylene glycol (Sloviter et al, 1962), albumin, dextran, sucrose, ethylene glycol, i-erythritol, D-ribitol, D-mannitol (Rowe et al, 1962), D-sorbitol, i-inositol, D-lactose, choline chloride (Rowe et al, 1962), amino acids (Phan The Tran et al, 1960a), methanol, acetamide, glycerol monoacetate (Lovelock, 1954), inorganic salts (Phan The Tran et al, 1960b; Phan The Tran et al), and DMSO combined with hydroxyethyl starch and human serum albumin (Zaroulis et al, 1980).

A controlled cooling rate is critical. Different cryoprotective agents (Rapatz et al, 1968) and different cell types have different optimal cooling rates. See, e.g., Rowe et al (1962b); Rowe (1966); Lewis et al, (1967); and Mazur, (1970) for effects of cooling velocity on survival of cells and on their transplantation potential. The heat of fusion phase where water turns to ice should be minimal. The cooling procedure can be carried out by use of, e.g., a programmable freezing device or a methanol bath procedure.

Programmable freezing apparatuses allow determination of optimal cooling rates and facilitate standard reproducible cooling. Programmable controlled-rate freezers such as Cryomed or Planar permit tuning of the freezing regimen to the desired cooling rate curve.

After thorough freezing, cells can be rapidly transferred to a long-term cryogenic storage vessel. In one embodiment, samples can be cryogenically stored in mechanical freezers, such as freezers that maintain a temperature of about −80° C. or about −20° C. In a preferred embodiment, samples can be cryogenically stored in liquid nitrogen (−196° C.) or its vapor. Such storage is greatly facilitated by the availability of highly efficient liquid nitrogen refrigerators, which resemble large Thermos containers with an extremely low vacuum and internal super insulation, such that heat leakage and nitrogen losses are kept to an absolute minimum.

Considerations and procedures for the manipulation, cryopreservation, and long term storage of T cells can be found, for example, in the following references, incorporated by reference herein: Gorin (1986) and International Atomic Energy Agency (1969).

Other methods of cryopreservation of viable cells, or modifications thereof, are available and envisioned for use, e.g., cold metal-mirror techniques. See Livesey et al (1987); Linner et al (1986); see also U.S. Pat. No. 4,199,022 by Senken et al, U.S. Pat. No. 3,753,357 by Schwartz, and U.S. Pat. No. 4,559,298 by Fahy.

Frozen cells are preferably thawed quickly (e.g., in a water bath maintained at 37-47° C.) and chilled immediately upon thawing. It may be desirable to treat the cells in order to prevent cellular clumping upon thawing. To prevent clumping, various procedures can be used, including but not limited to the addition before or after freezing of DNAse (Spitzer et al, 1980), low molecular weight dextran and citrate, citrate, hydroxyethyl starch (Stiff et al, 1983), or acid citrate dextrose (Zaroulis et al, 1980), etc.

The cryoprotective agent, if toxic in humans, should be removed prior to therapeutic use of the thawed T cells. One way in which to remove the cryoprotective agent is by dilution to an insignificant concentration.

Once frozen T cells have been thawed and recovered, they are used to promote neuronal regeneration as described herein with respect to non-frozen T cells. Once thawed, the T cells may be used immediately, assuming that they were activated prior to freezing. Preferably, however, the thawed cells are cultured before injection to the patient in order to eliminate non-viable cells. Furthermore, in the course of this culturing over a period of about one to three days, an appropriate activating agent can be added so as to activate the cells, if the frozen cells were resting T cells, or to help the cells achieve a higher rate of activation if they were activated prior to freezing. Usually, time is available to allow such a culturing step prior to administration as the T cells may be administered as long as a week after injury, and possibly longer, and still maintain their neuroregenerative and neuroprotective effect.

(2) Cop 1 and Cop 1-Related Peptides and Polypeptides

Pharmaceutical compositions comprising Cop 1 or a Cop 1-related peptide or polypeptide antigen or derivative thereof can be used for preventing or inhibiting the effects of injury or disease that result in NS degeneration, for promoting nerve regeneration in the NS, particularly in the CNS, for protecting CNS cells from glutamate toxicity, or for treating injury or disease caused or exacerbated by glutamate toxicity. Additionally, Cop 1 or a Cop 1-related peptide or polypeptide antigen or derivative thereof may be used for in vivo or in vitro activation of T cells. In one embodiment, methods of promoting nerve regeneration or of preventing or inhibiting the effects of CNS or PNS injury or disease comprise administering Cop 1 or a Cop 1-related peptide or polypeptide antigen or derivative thereof to a mammal wherein the Cop 1 or Cop 1-related peptide or polypeptide antigen or derivative thereof activates T cells in vivo to produce a population of T cells that accumulates at a site of injury or disease of the CNS or PNS. In another embodiment, Cop 1 or a Cop 1-related peptide or polypeptide antigen or derivative thereof is administered in methods for protecting CNS cells from glutamate toxicity or for treating disease injury or caused or exacerbated by glutamate toxicity.

The composition for use in the present invention can be Cop 1 or a Cop 1-related peptide or polypeptide. For the purpose of the present invention, "Cop 1 or a Cop 1-related peptide or polypeptide" is intended to include any peptide or polypeptide, including a random copolymer, that cross-reacts functionally with myelin basic protein (MBP) and is able to compete with MBP on the MHC class II in the antigen presentation.

The composition may comprise random copolymers comprising a suitable quantity of an amino acid of positive electrical charge, such as lysine or arginine, in combination with an amino acid with a negative electrical charge (preferably in a lesser quantity), such as glutamic acid or aspartic acid, optionally in combination with an electrically neutral amino acid such as alanine or glycine, serving as a filler, and optionally with an amino acid adapted to confer on the copolymer immunogenic properties, such as an aromatic amino acid like tyrosine or tryptophan. Such compositions may include any of those disclosed in WO 005250, the entire contents of which being hereby incorporated herein by reference.

More specifically, the composition for use in the present invention comprises at least one copolymer selected from the group consisting of random copolymers comprising one amino acid selected from each of at least three of the following groups:

(a) lysine and arginine;
(b) glutamic acid and aspartic acid;
(c) alanine and glycine;
(d) tyrosine and tryptophan.

The copolymers for use in the present invention can be composed of L- or D-amino acids or mixtures thereof. As is known by those of skill in the art, L-amino acids occur in most natural proteins. However, D-amino acids are commercially available and can be substituted for some or all of the amino acids used to make the terpolymers and other copolymers of the present invention. The present invention contemplates copolymers containing both D- and L-amino acids, as well as copolymers consisting essentially of either L- or D-amino acids.

In one embodiment of the invention, the copolymer contains four different amino acids, each from a different one of the groups (a) to (d). A preferred copolymer according to this embodiment of the present invention comprises in combination alanine, glutamic acid, lysine, and tyrosine, of net overall positive electrical charge and of a molecular weight of about 2,000 to about 40,000 daltons, preferably of about 2,000 to about 13,000 daltons. The most preferred example is Copolymer 1 (Cop 1) of average molecular weight about 4,700 to about 13,000 daltons. Preferred molecular weight ranges and processes for making a preferred form of Copolymer 1 are described in U.S. Pat. No. 5,800,808, the entire contents of which being hereby incorporated in the entirety. It is clear that this is given by way of example only, and that the composition can be varied both with respect to the constituents and relative proportions of the constituents if the above general criteria are adhered to. Thus, the copolymer may be a polypeptide from about 15 to about 100, preferably from about 40 to about 80, amino acids in length.

In another embodiment, the copolymer contains three different amino acids each from a different one of three groups of the groups (a) to (d). These copolymers are herein referred to as terpolymers.

In one embodiment, the terpolymers for use in the present invention contain tyrosine, alanine, and lysine, hereinafter designated YAK. The average molar fraction of the amino acids in these terpolymers can vary. For example, tyrosine can be present in a mole fraction of about 0.005 to about 0.250; alanine can be present in a mole fraction of about 0.3 to about 0.6; and lysine can be present in a mole fraction of about 0.1 to about 0.5. The average molecular weight is between 2,000 to about 40,000 daltons, and preferably between about 3,000 to about 35,000 daltons. In a more preferred embodiment, the average molecular weight is about 5,000 to about 25,000 daltons. It is possible to substitute arginine for lysine, glycine for alanine, and/or tryptophan for tyrosine.

In another embodiment, the terpolymers for use in the present invention contain tyrosine, glutamic acid, and lysine, hereinafter designated YEK. The average molar fraction of the amino acids in these terpolymers can vary: glutamic acid can be present in a mole fraction of about 0.005 to about 0.300, tyrosine can be present in a mole fraction of about 0.005 to about 0.250, and lysine can be present in a mole fraction of about 0.3 to about 0.7. The average molecular weight is between 2,000 and about 40,000 daltons, and preferably between about 3,000 and about 35,000 daltons. In a more preferred embodiment, the average molecular weight is about 5,000 to about 25,000 daltons. It is possible to substitute aspartic acid for glutamic acid, arginine for lysine, and/or tryptophan for tyrosine.

In another embodiment the terpolymers for use in the present invention contain lysine, glutamic acid, and alanine, hereinafter designated KEA. The average molar fraction of the amino acids in these polypeptides can also vary. For example, glutamic acid can be present in a mole fraction of about 0.005 to about 0.300, alanine can be present in a mole fraction of about 0.005 to about 0.600, lysine can be present in a mole fraction of about 0.2 to about 0.7. The average molecular weight is between 2,000 and 40,000 daltons, and preferably between about 3,000 and 35,000 daltons. In a more preferred embodiment, the average molecular weight is about 5,000 to about 25,000 daltons. It is possible to substitute aspartic acid for glutamic acid, glycine for alanine, and/or arginine for lysine.

In another embodiment, the terpolymers for use in the present invention contain tyrosine, glutamic acid, and alanine, hereinafter designated YEA. The average molar fraction of the amino acids in these polypeptides can vary. For example, tyrosine can be present in a mole fraction of about 0.005 to about 0.250, glutamic acid can be present in a mole fraction of about 0.005 to about 0.300, and alanine can be present in a mole fraction of about 0.005 to about 0.800. The average molecular weight is between 2,000 and about 40,000 daltons, and preferably between about 3,000 and about 35,000 daltons. In a more preferred embodiment, the average molecular weight is about 5,000 to about 25,000 daltons. It is possible to substitute tryptophan for tyrosine, aspartic acid for glutamic acid, and/or glycine for alanine.

In a more preferred embodiment, the mole fraction of amino acids of the terpolymers is about what is preferred for Copolymer 1. The mole fraction of amino acids in Copolymer 1 is glutamic acid about 0.14, alanine about 0.43, tyrosine about 0.10, and lysine about 0.34. The most preferred average molecular weight for Copolymer 1 is between about 5,000 and about 9,000 daltons. The activity of Copolymer 1 for the utilities disclosed herein is expected to remain if one or more of the following substitutions is made: aspartic acid for glutamic acid, glycine for alanine, arginine for lysine, and tryptophan for tyrosine.

The molar ratios of the monomers of the more preferred terpolymer of glutamic acid, alanine, and tyrosine, or YEA, is about 0.21 to about 0.65 to about 0.14.

The molar ratios of the monomers of the more preferred terpolymer of glutamic acid, alanine and lysine, or KEA, is about 0.15 to about 0.48 to about 0.36.

The molar ratios of the monomers of the more preferred terpolymer of glutamic acid, tyrosine, and lysine, or YEK, is about 0.26 to about 0.16 to about 0.58.

The molar ratios of the monomers of the more preferred terpolymer of tyrosine, alanine and lysine, or YAK, is about 0.10 to about 0.54 to about 0.35.

The terpolymers can be made by any procedure available to one of skill in the art. For example, the terpolymers can be made under condensation conditions using the desired molar ratio of amino acids in solution, or by solid phase synthetic procedures. Condensation conditions include the proper temperature, pH, and solvent conditions for condensing the carboxyl group of one amino acid with the amino group of another amino acid to form a peptide bond. Condensing agents, for example dicyclohexyl-carbodiimide, can be used to facilitate the formation of the peptide bond. Blocking groups can be used to protect functional groups, such as the side chain moieties and some of the amino or carboxyl groups against undesired side reactions.

For example, the process disclosed in U.S. Pat. No. 3,849,650, can be used wherein the N-carboxyanhydrides of tyrosine, alanine, γ-benzyl glutamate and N ε-trifluoroacetyl-lysine are polymerized at ambient temperatures in anhydrous dioxane with diethylamine as an initiator. The γ-carboxyl group of the glutamic acid can be deblocked by hydrogen bromide in glacial acetic acid. The trifluoroacetyl groups are removed from lysine by 1 molar piperidine. One of skill in the art readily understands that the process can be adjusted to make peptides and polypeptides containing the desired amino acids, that is, three of the four amino acids in Copolymer 1, by selectively eliminating the reactions that relate to any one of glutamic acid, alanine, tyrosine, or lysine. For purposes of this application, the terms "ambient temperature" and "room temperature" mean a temperature ranging from about 20 to about 26° C.

The molecular weight of the terpolymers can be adjusted during polypeptide synthesis or after the terpolymers have been made. To adjust the molecular weight during polypeptide synthesis, the synthetic conditions or the amounts of amino acids are adjusted so that synthesis stops when the polypeptide reaches the approximate length which is desired. After synthesis, polypeptides with the desired molecular weight can be obtained by any available size selection procedure, such as chromatography of the polypeptides on a molecular weight sizing column or gel, and collection of the molecular weight ranges desired. The present polypeptides can also be partially hydrolyzed to remove high molecular weight species, for example, by acid or enzymatic hydrolysis, and then purified to remove the acid or enzymes.

In one embodiment, the terpolymers with a desired molecular weight may be prepared by a process which includes reacting a protected polypeptide with hydrobromic acid to form a trifluoroacetyl-polypeptide having the desired molecular weight profile. The reaction is performed for a time and at a temperature which is predetermined by one or more test reactions. During the test reaction, the time and temperature are varied and the molecular weight range of a given batch of test polypeptides is determined. The test conditions which provide the optimal molecular weight range for that batch of polypeptides are used for the batch. Thus, a trifluoroacetyl-polypeptide having the desired molecular weight profile can be produced by a process which includes reacting the protected polypeptide with hydrobromic acid for a time and at a temperature predetermined by test reaction. The trifluoroacetyl-polypeptide with the desired molecular weight profile is then further treated with an aqueous piperidine solution to form a low toxicity polypeptide having the desired molecular weight.

In a preferred embodiment, a test sample of protected polypeptide from a given batch is reacted with hydrobromic acid for about 10-50 hours at a temperature of about 20-28° C. The best conditions for that batch are determined by running several test reactions. For example, in one embodiment, the protected polypeptide is reacted with hydrobromic acid for about 17 hours at a temperature of about 26° C.

As binding motifs of Cop 1 to MS-associated HLA-DR molecules are known (Fridkis-Hareli et al, 1999b), polypeptides of fixed sequence can readily be prepared and tested for binding to the peptide binding groove of the HLA-DR molecules as described in the Fridkis-Hareli et al (1999b) publication. Examples of such peptides are those disclosed in WO 005249, the entire contents of which being hereby incorporated herein by reference. Thirty-two of the peptides specifically disclosed in said application are reproduced in Table 1, hereinbelow. Such peptides, and other similar peptides would be expected to have similar activity as Cop 1. However, this can readily be determined by testing for their ability to activate T cells in accordance with the present invention. All of this can be done without undue experimentation. Such peptides, and other similar peptides, are also considered to be within the definition of Cop 1-related peptides or polypeptides and their use is considered to be part of the present invention.

TABLE 1

| SEQ ID NO. | Peptide Sequence |
| --- | --- |
| 1 | AAAYAAAAAAKAAAA |
| 2 | AEKYAAAAAAKAAAA |

TABLE 1-continued

| SEQ ID NO. | Peptide Sequence |
|---|---|
| 3 | AKEYAAAAAAKAAAA |
| 4 | AKKYAAAAAAKAAAA |
| 5 | AEAYAAAAAAKAAAA |
| 6 | KEAYAAAAAAKAAAA |
| 7 | AEEYAAAAAAKAAAA |
| 8 | AAEYAAAAAAKAAAA |
| 9 | EKAYAAAAAAKAAAA |
| 10 | AAKYEAAAAAKAAAA |
| 11 | AAKYAEAAAAKAAAA |
| 12 | EAAYAAAAAAKAAAA |
| 13 | EKKYAAAAAAKAAAA |
| 14 | EAKYAAAAAAKAAAA |
| 15 | AEKYAAAAAAAAAA |
| 16 | AKEYAAAAAAAAAA |
| 17 | AKKYAAAAAAAAAA |
| 18 | AKKYAEAAAAAAAA |
| 19 | AEAYKAAAAAAAAA |
| 20 | KEAYAAAAAAAAAA |
| 21 | AEEYKAAAAAAAAA |
| 22 | AAEYKAAAAAAAAA |
| 23 | EKAYAAAAAAAAAA |
| 24 | AAKYEAAAAAAAAA |
| 25 | AAKYAEAAAAAAAA |
| 26 | EKKYAAAAAAAAAA |
| 27 | EAKYAAAAAAAAAA |
| 28 | AEYAKAAAAAAAAA |
| 29 | AEKAYAAAAAAAAA |
| 30 | EKYAAAAAAAAAAA |
| 31 | AYKAEAAAAAAAAA |
| 32 | AKYAEAAAAAAAAA |

The preferred copolymer for use in the present invention is Copolymer 1, herein referred to also as Cop 1. Copolymer 1 has been approved in several countries for the treatment of multiple sclerosis (MS) under the trade name, COPAXONE®, Glatiramer acetate. COPAXONE® is a trademark of Teva Pharmaceuticals Ltd., Petah Tikva, Israel. Several clinical trials demonstrated that Copolymer 1 is well tolerated with only minor side reactions which were mostly mild reactions at the injection site (Johnson et al, 1995).

(3) Therapeutic Uses

The compositions described in Sections (1) through (2) may be used to promote nerve regeneration or to prevent or inhibit secondary degeneration which may otherwise follow primary NS injury, e.g., closed head injuries and blunt trauma, such as those caused by participation in dangerous sports, penetrating trauma, such as gunshot wounds, hemorrhagic stroke, ischemic stroke, glaucoma, cerebral ischemia, or damages caused by surgery such as tumor excision. In addition, such compositions may be used to ameliorate the effects of disease that result in a degenerative process, e.g., degeneration occurring in either gray or white matter (or both) as a result of various diseases or disorders, including, without limitation: diabetic neuropathy, senile dementias, Alzheimer's disease, Parkinson's Disease, facial nerve (Bell's) palsy, glaucoma, Huntington's chorea, amyotrophic lateral sclerosis (ALS), status epilepticus, non-arteritic optic neuropathy, intervertebral disc herniation, vitamin deficiency, prion diseases such as Creutzfeldt-Jakob disease, carpal tunnel syndrome, peripheral neuropathies associated with various diseases, including but not limited to, uremia, porphyria, hypoglycemia, Sjorgren Larsson syndrome, acute sensory neuropathy, chronic ataxic neuropathy, biliary cirrhosis, primary amyloidosis, obstructive lung diseases, acromegaly, malabsorption syndromes, polycythemia vera, IgA and IgG gammapathies, complications of various drugs (e.g., metronidazole) and toxins (e.g., alcohol or organophosphates), Charcot-Marie-Tooth disease, ataxia telangectasia, Friedreich's ataxia, amyloid polyneuropathies, adrenomyeloneuropathy, Giant axonal neuropathy, Refsum's disease, Fabry's disease, lipoproteinemia, etc. In light of the findings with respect to the glutamate protective aspect of the present invention, other clinical conditions that may be treated in accordance with the present invention include epilepsy, amnesia, anxiety, hyperalgesia, psychosis, seizures, abnormally elevated intraocular pressure, oxidative stress, and opiate tolerance and dependence. In addition, the glutamate protective aspect of the present invention, i.e., treating injury or disease caused or exacerbated by glutamate toxicity, can include post-operative treatments such as for tumor removal from the CNS and other forms of surgery on the CNS.

In view of the fact that Cop 1 immunization has been surprisingly found useful in protecting against glutamate toxicity, it is expected that Cop 1 treatment or Cop 1-related T cell treatment in accordance with the present invention will be effective in the treatment of the above listed conditions not only in a late phase when myelin is being affected, but also in the early stages in which the neurons are being attacked by factors which cause an elevation in glutamate levels to toxic levels. Thus, the present invention is useful for any indication, i.e., chronic or acute neurodegeneration, which is caused or exacerbated by an elevation in glutamate levels, including the early stages of ischemic stroke, Alzheimer's disease, etc.

Furthermore, this glutamate toxicity protection establishes that the role of Cop 1 is not limited to its cross-reactivity with myelin. It must also have a regulatory activity, such as by creating regulatory cells or regulatory substances. In view of this regulatory activity, the Cop 1 vaccination and the Cop-1 specific activated T cells are expected also to protect white matter and gray matter from damage caused by oxidative stress and other sources of damage to neural cells. In addition, because of this regulatory activity, the present invention can also be used to protect neural cells not only from multiple sclerosis, as has been suggested in the prior art, but also from autoimmune diseases other than multiple sclerosis.

In a preferred embodiment, the activated T cells or immunization composition comprising Cop 1 or a Cop 1-related peptide or polypeptide of the present invention are used to treat diseases or disorders where promotion of nerve regeneration or prevention or inhibition of secondary neural degeneration is indicated, but excluding multiple sclerosis and neoplasias. In a preferred embodiment, the compositions of the present invention are administered to a human subject.

As disclosed hereinabove, Cop 1 has been used as an agent to achieve suppression or deactivation of autoimmune T cell reactivity to myelin antigens in multiple sclerosis patients. For that purpose, Cop 1 has been administered without adjuvants by daily subcutaneous injection. The prior art also discloses the administration of Cop 1 to multiple sclerosis patients by the oral route, which is also aimed at inducing suppression of the autoimmune T cell response to myelin antigens. Note that these uses of Cop 1 in the prior art of treatment for multiple sclerosis are fundamentally different from the use of Cop 1 for neuroprotection, which is the subject of the present invention. Firstly, as shown in WO99/60021 from the laboratory of the present inventors, neuroprotection is mediated by the activation of autoimmune T cells specifically directed to myelin antigens. Hence, it is most surprising that Cop 1, an agent designed to suppress T cell autoimmunity, should have an effect that requires activation of specific anti-myelin T cell autoimmunity. Secondly, the use of Cop 1 for neuroprotection in accordance with the present invention is based on the administration of anti-Cop 1 T cells, which is not the way that Cop 1 is used for treating multiple sclerosis. Thirdly, in a preferred embodiment, the present invention contemplates the use of Cop 1 administered in adjuvants, such as incomplete Freund's adjuvant or complete Freund's adjuvant, which is a type of Cop 1 preparation that has not been used previously for the treatment of multiple sclerosis or for any other therapeutic purpose. While the present invention contemplates oral administration of Cop 1 for neuroprotection, this is always subsequent to primary activation with Cop 1, preferably in adjuvant. Thus, oral Cop 1 can be used to boost the activity of the T cells subsequent to primary activation with Cop 1.

Accordingly, the composition and its mode of action and neuroprotection are novel, both practically and conceptually. It would not be obvious to one of ordinary skill in the art, familiar with the use of Cop 1 to suppress or deactivate T cell reactivity to myelin antigens, to use Cop 1 in a way specifically designed to activate T cells specifically directed to myelin antigens for their beneficial effect in neuroprotection, including ameliorating the degenerative process caused by autoimmune diseases.

Cop 1-activated T cells may also be used to ameliorate the degenerative process caused by neoplasms, without using immunotherapy processes. T cells activated with Cop 1 will accumulate at the site of neural degeneration and facilitate inhibition of this degeneration.

(4) Formulations and Administration

Pharmaceutical compositions for use in accordance with the present invention may be formulated in conventional manner using one or more physiologically acceptable carriers or excipients. The carrier(s) must be "acceptable" in the sense of being compatible with the other ingredients of the composition and not deleterious to the recipient thereof.

The following exemplification of carriers, modes of administration, dosage forms, etc., are listed as known possibilities from which the carriers, modes of administration, dosage forms, etc., may be selected for use with the present invention. Those of ordinary skill in the art will understand, however, that any given formulation and mode of administration selected should first be tested to determine that it achieves the desired results. Thus, for example, when the active principle is Cop 1 or a Cop 1-related peptide or polypeptide, the particular formulation and mode of administration must permit the active principle to act as a vaccine so as to raise T cells activated thereagainst in vivo. If such an immune response is not obtained, then that particular formulation and mode of administration should not be used in accordance with the present invention.

Similarly, if the active principle is activated T cells, then the particular formulation and mode of administration should be tested to ensure that the active T cells being administered reach the bloodstream in an active state so that they can home to the site of injury in the CNS in accordance with the present invention.

The term "carrier" refers to a diluent, adjuvant, excipient, or vehicle with which the therapeutic is administered. The carriers in the pharmaceutical composition may comprise a binder, such as microcrystalline cellulose, polyvinylpyrrolidone (polyvidone or povidone), gum tragacanth, gelatin, starch, lactose or lactose monochydrate; a disintegrating agent, such as alginic acid, maize starch and the like; a lubricant or surfactant, such as magnesium stearate, or sodium lauryl sulphate; a glidant, such as colloidal silicon dioxide; a sweetening agent, such as sucrose or saccharin; and/or a flavoring agent, such as peppermint, methyl salicylate, or orange flavoring.

Methods of administration include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the active compound.

For buccal administration, the compositions may take the form of tablets or lozenges formulated in conventional manner.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

The compositions may also be formulated in rectal compositions such as suppositories or retention enemas, e.g., containing conventional suppository bases such as cocoa butter or other glycerides.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

In a preferred embodiment, compositions comprising Cop 1-activated T cells, a Cop 1 or a Cop 1-related peptide or polypeptide are formulated in accordance with routine procedures as pharmaceutical compositions adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together. Where the composition is to be administered by infusion, it can be dispensed with an infusion bottle containing sterile pharmaceutical grade water or saline. Where the composition is administered by injection, an ampoule of sterile water or saline for injection can be provided so that the ingredients may be mixed prior to administration.

Pharmaceutical compositions comprising Cop 1 or Cop 1-related peptide or polypeptide may optionally be administered with an adjuvant in the usual manner for immunization. Non-limiting examples of such adjuvants include alum and incomplete Freund's adjuvant. Other manners of improving the immunogenicity of the administered peptide or polypeptide include administration in the form of an aggregation or a complex with albumin or with other carriers, all as are well known to those of ordinary skill in the vaccine art. Metabolizable lipid emulsions, such as Intralipid or Lipofundin may also be used as vehicles for the Cop 1 therapy in the manner disclosed in WO 97/02016, the entire contents of which being hereby incorporated herein by reference. While these materials are known to cause a TH1 to TH2 cytokine shift, there is no reason to believe that TH2 cytokines will not be operable, and perhaps even preferable, for the purpose of the present invention.

When Cop 1 is introduced orally, it may be mixed with other food forms and consumed in solid, semi-solid, suspension, or emulsion form; and it may be mixed with pharmaceutically acceptable carriers, including water, suspending agents, emulsifying agents, flavor enhancers, and the like. In one embodiment, the oral composition is enterically-coated. Use of enteric coatings is well known in the art. For example, Lehman (1971) teaches enteric coatings such as Eudragit S and Eudragit L. The *Handbook of Pharmaceutical Excipients, 2nd* Ed., also teaches Eudragit S and Eudragit L applications. One Eudragit which may be used in the present invention is L30D55.

Cop 1 may also be administered nasally in certain of the above-mentioned forms by inhalation or nose drops. Furthermore, oral inhalation may be employed to deliver Cop 1 to the mucosal linings of the trachea and bronchial passages.

The invention also provides a pharmaceutical pack or kit comprising one or more containers filled with one or more of the ingredients of the pharmaceutical compositions of the invention.

In a preferred embodiment, the pharmaceutical compositions of the invention are administered to a mammal, preferably a human, shortly after injury or detection of a degenerative lesion in the NS. The therapeutic methods of the invention may comprise administration of Cop 1-activated T cells or Cop 1 or Cop 1-related peptide or polypeptide, or any combination thereof. When using combination therapy, Cop 1 may be administered before, concurrently or after administration of Cop 1-activated T cells.

In one embodiment, the compositions of the invention are administered in combination with one or more of the following (a) mononuclear phagocytes, preferably cultured monocytes (as described in PCT publication No. WO 97/09985, which is incorporated herein by reference in its entirety), that have been stimulated to enhance their capacity to promote neuronal regeneration; (b) a neurotrophic factor such as acidic fibroblast growth factor; and (c) an anti-inflammatory therapeutic substance (i.e., an anti-inflammatory steroid, such as dexamethasone or methylprednisolone, or a non-steroidal anti-inflammatory peptide, such as Thr-Lys-Pro (TKP)).

In another embodiment, mononuclear phagocyte cells according to PCT Publication No. WO 97/09985 and U.S. Pat. No. 6,267,995, are injected into the site of injury or lesion within the CNS, either concurrently, prior to, or following parenteral administration of Cop 1-activated T cells, Cop 1 or a Cop 1-related peptide or polypeptide.

In another embodiment, administration of Cop-activated T cells, Cop 1 or a Cop 1-related peptide or polypeptide, may be administered as a single dose or may be repeated, preferably at 2 week intervals and then at successively longer intervals once a month, once a quarter, once every six months, etc. The course of treatment may last several months, several years or occasionally also through the life-time of the individual, depending on the condition or disease which is being treated. In the case of a CNS injury, the treatment may range between several days to months or even years, until the condition has stabilized and there is no or only a limited risk of development of secondary degeneration. In chronic human disease or Parkinson's disease, the therapeutic treatment in accordance with the invention may be for life.

As will be evident to those skilled in the art, the therapeutic effect depends at times on the condition or disease to be treated, on the individual's age and health condition, on other physical parameters (e.g., gender, weight, etc.) of the individual, as well as on various other factors, e.g., whether the individual is taking other drugs, etc.

The optimal dose of the therapeutic compositions comprising Cop 1-activated T cells of the invention is proportional to the number of nerve fibers affected by NS injury or disease at the site being treated. In a preferred embodiment, the dose ranges from about $5 \times 10^6$ to about $10^7$ cells for treating a lesion affecting about $10^5$ nerve fibers, such as a complete transection of a rat optic nerve, and ranges from about $10^7$ to about $10^8$ cells for treating a lesion affecting about $10^{6-10^7}$ nerve fibers, such as a complete transection of a human optic nerve. As will be evident to those skilled in the art, the dose of T cells can be scaled up or down in proportion to the number of nerve fibers thought to be affected at the lesion or site of injury being treated

(5) Establishment of Autologous Cell Banks for T Lymphocytes

To minimize secondary damage after nerve injury, patients can be treated by administering autologous or semi-allogeneic T lymphocytes sensitized to Cop 1 or a Cop 1-related peptide or polypeptide. As the window of opportunity has not yet been precisely defined, therapy should be administered as soon as possible after the primary injury to maximize the chances of success, preferably within about one week.

To bridge the gap between the time required for activation and the time needed for treatment, a bank can be established with personal vaults of autologous T lymphocytes prepared for future use for neuroprotective therapy against secondary degeneration in case of NS injury. T lymphocytes are isolated from the blood and then sensitized to Cop 1 or a Cop 1-related peptide or polypeptide. The cells are then frozen and suitably stored under the person's name, identity number, and blood group, in a cell bank until needed.

Additionally, autologous stem cells of the CNS can be processed and stored for potential use by an individual patient in the event of traumatic disorders of the NS such as ischemia or mechanical injury, as well as for treated neurodegenerative conditions such as Alzheimer's disease or Parkinson's disease. Alternatively, semi-allogeneic or allogeneic T cells can be stored frozen in banks for use by any individual who shares one MHC type II molecule with the source of the T cells.

The following examples illustrate certain features of the present invention but are not intended to limit the scope of the present invention.

(6) EXAMPLES

Materials And Methods for Examples 1 and 2

Animals. Inbred female adult Lewis rats (8-12 weeks old) were supplied by the Animal Breeding Center of The Weizmann Institute of Science. The rats were housed in a light- and temperature-controlled room and matched for age in each experiment. Animals were handled according to the regulations formulated by IACUC (Institutional Animal Care and Use Committee).

Antigens. Myelin Basic Protein (MBP) from the spinal cords of guinea pigs and ovalbumin (OVA) were purchased from Sigma (St. Louis, Mo.). The Cop 1 used in the present examples was the COPAXONE® product of Teva Pharmaceuticals (Israel), which product was obtained commercially.

Antibodies. Mouse monoclonal anti rat T cell receptor (TCR) was kindly provided by Dr. Boris Reizis. Cy-3 conjugated goat anti mouse IgG (with minimal cross-reaction to rat, human, bovine, and horse serum proteins), was purchased from Jackson ImmunoResearch (West Grove, Pa.).

T Cell Lines. T cell lines were generated from draining lymph node cells obtained from Lewis rats immunized with the above antigens (Ben-Nun et al, 1981a). The antigen was dissolved in phosphate-buffered saline (PBS) (1 mg/ml) and emulsified with an equal volume of incomplete Freund's adjuvant (IFA) (Difco Laboratories, Detroit, Mich.) supplemented with 4 mg/ml *Mycobacterium tuberculosis* (Difco). Ten days after the antigen was injected into the rats' hind footpads in 0.1 ml of the emulsion, the rats were killed and their draining lymph nodes were surgically removed and dissociated. The cells were washed and activated with the antigen (10 µg/ml) in stimulation medium containing Dulbecco's modified Eagle's medium (DMEM) supplemented with L-glutamine (2 mM), 2-mercaptoethanol ($5\times10^5$ M), sodium pyruvate (1 mM), penicillin (100 IU/ml), streptomycin (100 µg/ml), non-essential amino acids (1 ml/100 ml), and autologous serum 1% (volume/volume). After incubation for 72 hours at 37° C., 98% relative humidity and 10% $CO_2$, the cells were transferred to propagation medium consisting of DMEM, L-glutamine, 2-mercaptoethanol, sodium pyruvate, non-essential amino acids, and antibiotics in the same concentrations as above, with the addition of 10% fetal calf serum (FCS) (volume/volume) and 10% T-cell growth factor derived from the supernatant of concanavalin A (ConA)-stimulated spleen cells (Gillis et al, 1978). Cells were grown in propagation medium for 4-10 days before being restimulated with their antigen (10 µg/ml) in the presence of irradiated (2000 rad) thymus cells ($10^7$ cells/ml) in stimulation medium. The T cell lines were expanded by repeated stimulation and propagation (Ben-Nun et al, 1982).

Crush Injury of Optic Nerve. The optic nerve was subjected to crush injury as previously described (Duvdevani et al, 1990). Briefly, rats were deeply anesthetized by intraperitoneal (i.p.) injection of Rompun (xylazine, 10 mg/kg; Vitamed, Israel) and Vetalar (ketamine, 50 mg/kg; Fort Dodge Laboratories, Fort Dodge, Iowa). Using a binocular operating microscope, lateral canthotomy was performed in the right eye, and the conjunctiva was incised lateral to the cornea. After separation of the retractor bulbi muscles, the optic nerve was exposed intraorbitally by blunt dissection. Using calibrated cross-action forceps, the optic nerve was subjected to a crush injury 1-2 mm from the eye. Mild and severe crush injuries were inflicted for short-term trials (two weeks), as this time period was shown to be optimal for demonstrating secondary degeneration and its response to treatment (Yoles, 1998). The uninjured contralateral nerve was left undisturbed.

Measurement of Secondary Degeneration by Retrograde Labeling of Retinal Ganglion Cells. Secondary degeneration of the optic nerve axons and their attached retinal ganglion cells (RGCs) was measured after post-injury application of the fluorescent lipophilic dye, 4-(4-(didecylamino)styryl)-N-methylpyridinium iodide (4-Di-10-Asp) (Molecular Probes Europe BV, Netherlands), distally to the lesion site, two weeks after crush injury. Because only axons that are intact can transport the dye back to their cell bodies, application of the dye distally to the lesion site after two weeks ensures that only axons that survived both the primary damage and the secondary degeneration will be counted. This approach enabled differentiation between neurons that are still functionally intact and neurons in which the axons are injured but the cell bodies are still viable, because only those neurons whose fibers are morphologically intact can take up dye applied distally to the site of injury and transport it to their cell bodies. Using this method, the number of labeled RGCs reliably reflects the number of still-functioning neurons. Labeling and measurement were carried out as follows: the right optic nerve was exposed for the second time, again without damaging the retinal blood supply. Complete axotomy was performed 1-2 mm from the distal border of the injury site and solid crystals (0.2-0.4 mm diameter) of 4-Di-10-Asp were deposited at the site of the newly formed axotomy. Five days after dye application the rats were killed. The retina was detached from the eye, prepared as a flattened whole mount in 4% paraformaldehyde solution, and examined for labeled RGCs by fluorescence microscopy.

Enzyme-linked Immunosorbent Assay. Anti-MBP T cells were grown for a week in a propagation medium, then washed with PBS and resuspended in stimulation medium. The T cells ($0.5\times10^6$ cells/ml) were incubated, in the presence of irradiated thymocytes ($10^7$ cells/ml), with ConA (1.25 µg/ml), or with MBP antigen (10 µg/ml), or with Cop 1 antigen (10 µg/ml), or with OVA antigen (10 µg/ml), or with no antigen, in stimulation medium at 37° C., 98% relative humidity and 10% $CO_2$. In addition, irradiated thymocytes ($10^7$ cells/ml) alone were incubated in stimulation medium. After 48 hours the cells were centrifuged and their supernatants were collected and sampled. Concentrations of neurotrophin (NT)-3, nerve growth factor (NGF), and NT-4/5 in the samples were determined by the use of sandwich enzyme-linked immunosorbent assay (ELISA) kits (Promega, Madison, Wis.) and comparison with a NT standard (absorbance measurement at 450 nm using an ELISA reader). Concentrations of brain-derived neurotrophic factor (BDNF) in the samples were determined with a sensitive sandwich ELISA. In brief, 96-well flat-bottomed plates were coated with a chicken anti-human BDNF antibody (Promega, Madison, Wis.) in 0.025 M $NaHCO_3$ and 0.025 M $Na_2CO_3$ (pH 8.2). Recombinant human BDNF (used as standard; Research Diagnostics, Flanders, N.J.) was used in serial dilutions in blocking solution containing 3% bovine serum albumin (BSA), 0.05% polyoxyethylene-sorbitan monolaurate (Tween-20), and 1% FCS in PBS (pH 8.2). Bound BDNF was detected by incubating the plates with a mouse anti-human BDNF antibody (Research Diagnostics) and then with peroxidase-conjugated goat anti-mouse IgG (Jackson ImmunoReasearch, West Grove, Pa.) in blocking solution. The plates were developed using a 3,3',5,5'-tetramethyl-benzidine liquid substrate system (Sigma, St. Louis, Mo.). The reaction was stopped by adding 1M $H_3PO_4$, and the optical density was determined at 450 nm. Results for each experiment were calculated as the amount of secreted NT per 1 ml of sample, after subtraction of the background levels of the irradiated thymocytes incubated with the stimulation medium.

Immunohistochemistry. Longitudinal cryosections (10 μm thick) of the nerves were picked up onto gelatin-coated glass slides and frozen until preparation for fluorescence staining. The sections were fixed in ethanol for 10 min at room temperature, washed twice with double-distilled water, and incubated for three minutes in PBS containing 0.05% Tween-20. Sections were then incubated for one hour at room temperature with mouse anti-rat monoclonal antibodies to TCR (Hunig, 1989) diluted in PBS containing 3% FCS and 2% BSA. The sections were then washed 3 times with PBS containing 0.05% Tween-20 and incubated with Cy3-conjugated goat anti-mouse IgG (with minimal cross-reaction to rat, human, bovine, and horse serum proteins; Jackson ImmunoResearch, West Grove, Pa.) for 1 h at room temperature. The sections were washed with PBS containing Tween-20 and treated with glycerol containing 1,4-diazobicyclo-(2,2,2) octane to inhibit quenching of fluorescence. The sections were viewed with a Zeiss Universal fluorescence microscope.

Example 1

Neuroprotection by Anti-cop 1 T Cells

Figure 1B:
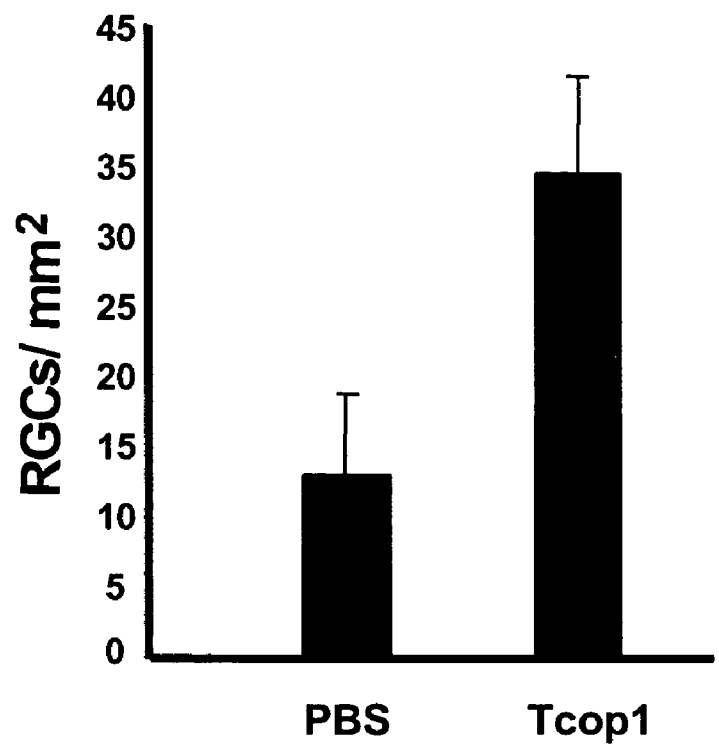

Adoptive Transfer of T Cells Reactive to Cop 1 is Neuroprotective in the Injured Optic Nerve In a previous study, from the laboratory of the present inventors, it was shown that after acute CNS trauma in the rat, passive transfer of encephalitogenic T cells specific to CNS self antigens such as MBP prevents the spread of damage and thus arrests secondary degeneration (see WO 99/60021). Here, the neuroprotective effect of T cells reactive to Cop 1 is demonstrated, which T cells, unlike MBP-reactive T cells, are not encephalitogenic. Immediately after mild (FIG. 1A) or severe (FIG. 1B) optic nerve injury, rats were injected with PBS in IFA or with Cop 1-specific T cells in IFA. For assessment of secondary degeneration, the neurotracer dye 4-Di-10-Asp was applied to the optic nerve distal to the site of injury, two weeks after the injury. After five days, the rats were killed and their retinas were excised and flat-mounted. Labeled (surviving) RGCs, from four fields located at approximately the same distance from the optic disk in each retina, were counted under a fluorescence microscope. The results are shown in FIGS. 1A and 1B. The neuroprotective effect of Cop 1-reactive T cells compared with that of PBS was significant for both mild crush injury ($P<0.005$, Student's t-test) and severe crush injury ($P<0.05$, Student's t-test). The results are the summary of three experiments. Each group contained six to ten rats.

Cop 1-Reactive T Cells Accumulate in Both Injured and Non-injured Neuronal Tissues The laboratory of the present inventors has previously shown that the passive transfer of anti-MBP T cells into crush-injured rats is followed by a massive accumulation of the injected T cells at the site of injury. The passive transfer of Cop 1-reactive T cells in the present study also caused a significant accumulation of the injected T cells at the site of injury relative to the accumulation of endogenous anti-MBP T cells in the PBS-treated injured rats. T cell accumulation in the Cop 1-treated rats was greatest on day 7 after the injection. These findings were in line with the earlier results with injected T cell lines of different specificities. In that study, T cell accumulation at the site of the lesion in injured nerves was non-selective, in contrast to uninjured nerves, where only T cells specific to CNS self antigens were found to accumulate. Therefore, accumulation of T cells to Cop 1 in the injured nerve does not provide any indication for cross-recognition with any of the resident CNS proteins and thus for activity. However, T cells to Cop 1, similarly to T cells to MBP, did accumulate in the non-injured nerve, unlike T cells to OVA (results not shown). Although there was less accumulation of T cells reactive to Cop 1 than of T cells specific to MBP, these findings further support the notion of cross-reactivity between Cop 1 and MBP in vivo.

Cytokine and Neurotrophin Profiles of Injected T Cell Lines Specific to MBP and to Cop 1

Supernatants from unstimulated T cells or from T cells stimulated for 48 hours with ConA mitogen, or MBP antigen, or Cop 1 antigen in stimulation medium were subjected to sandwich ELISA. The cultured media containing products secreted by these cells were collected and their cytokine contents were quantified by ELISA. The results are shown in Table 2. The activated T cells secreted much larger amounts of cytokines than did the unstimulated T cells. The MBP-stimulated T cells preferentially expressed the Th1-specific cytokine INF whereas the Cop 1-stimulated T cells preferentially expressed the Th2-specific cytokine IL-10. The largest amounts of secreted cytokines were detected in the supernatants of T cells stimulated with ConA (Table 2).

TABLE 2

|  | Resting State | | Stimulation with MBP | | Stimulation with Cop 1 | | Stimulation with ConA | |
| --- | --- | --- | --- | --- | --- | --- | --- | --- |
|  | Tmbp | Tcop | Tmbp | Tcop | Tmbp | Tcop | Tmbp | Tcop |
| IFN-γ (pgr/ml) | 725 | 6645 | 15692 | 925 | 7242 | 11825 | 22758 | 22525 |
| IL-10 (pgr/ml) | 41 | 382 | 1941 | 13 | 365 | 7244 | 3565 | 6503 |

Figure 2A:
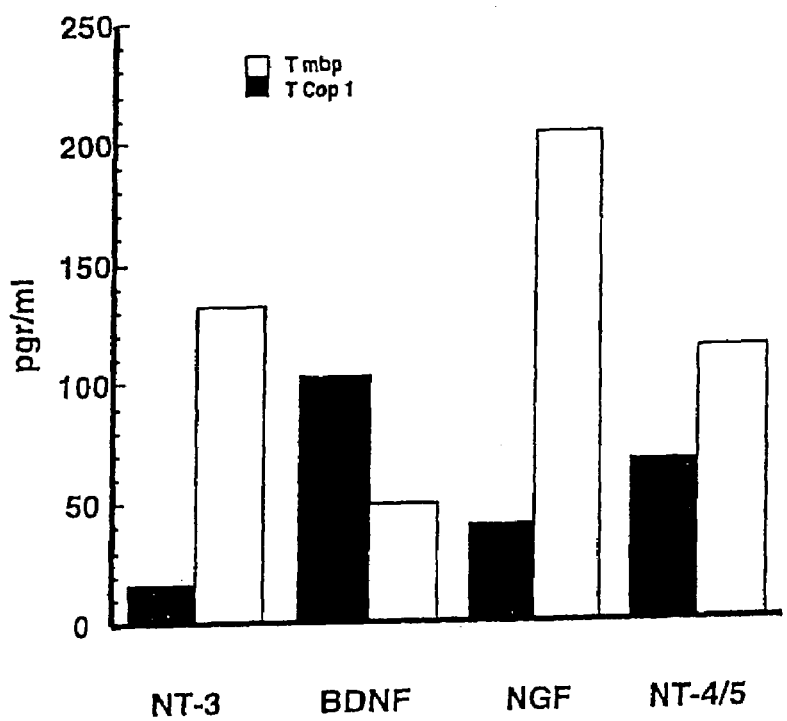
FIGS. 2A and 2B are graphs representing the ELISA of secreted neurotrophic factors. Rat anti-MBP (white bars in FIG. 2A) or anti-Cop 1 (black bars in FIG. 2A) T cells were cultured for 48 hours with their specific antigen in stimulation medium. The T cell supernatants were collected and subjected to sandwich ELISA. The graph shows the concentration of NT3, BDNF, NGF and NT-4/5 secreted in each sample. The ratios of the amounts of BDNF or NT-3 secreted by anti-Cop 1 T cells to the amounts secreted by anti-MBP T cells are shown in FIG. 2B. The mean ratios ±SD of five independent experiments with neurotrophin (NT) are shown.
Figure 2B:
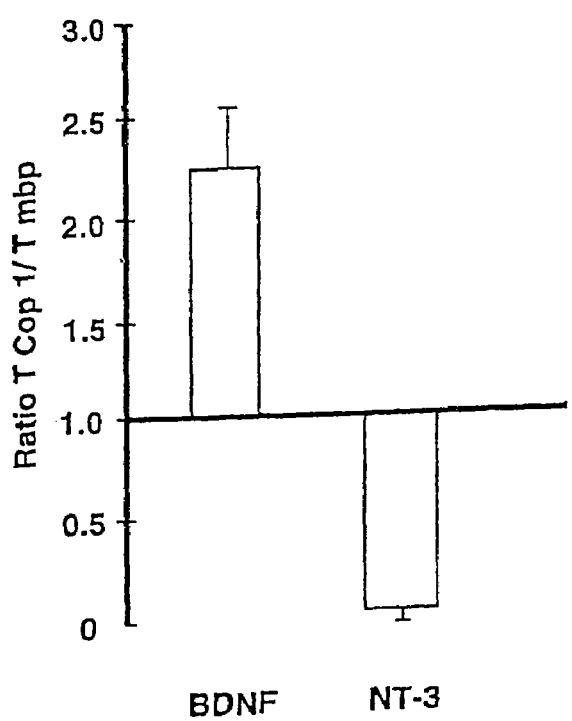

Up-regulation of neurotrophic expression and secretion by T cells activated with their specific antigens was recently demonstrated in the laboratory of the present inventors. In an attempt to gain an insight into the mechanism underlying T cell-mediated neuroprotection, the T cell supernatants in the present study were subjected to ELISA to determine the neurotrophin (NT) profiles of T cells responsible for neuroprotection. The Cop 1-stimulated T cells secreted both NGF and NT-4/5, but in lower amounts than those secreted by the anti-MBP T cells. Relative to the production by anti-MBP T cells, the production of NT-3 by the Cop 1-stimulated T cells was insignificant; the production of BDNF, however, was massive (FIG. 2A). Thus, the Cop 1-stimulated T cells produced smaller amounts of all of the examined neurotrophic factors, with the notable exception of BDNF (FIG. 2A). Four independent determinations of the amounts of NT-3 and BDNF secreted by the differentially stimulated T cells yielded similar results. In each case, Cop 1-stimulated T cells produced about 2.5-fold more BDNF than anti-MBP T cells, and only 10% of the amounts of NT-3 (FIG. 2B).

Example 2

Vaccination with Cop 1

Vaccination with Cop 1 Protects Optic Nerve Fibers from Secondary Degeneration

Figure 3:
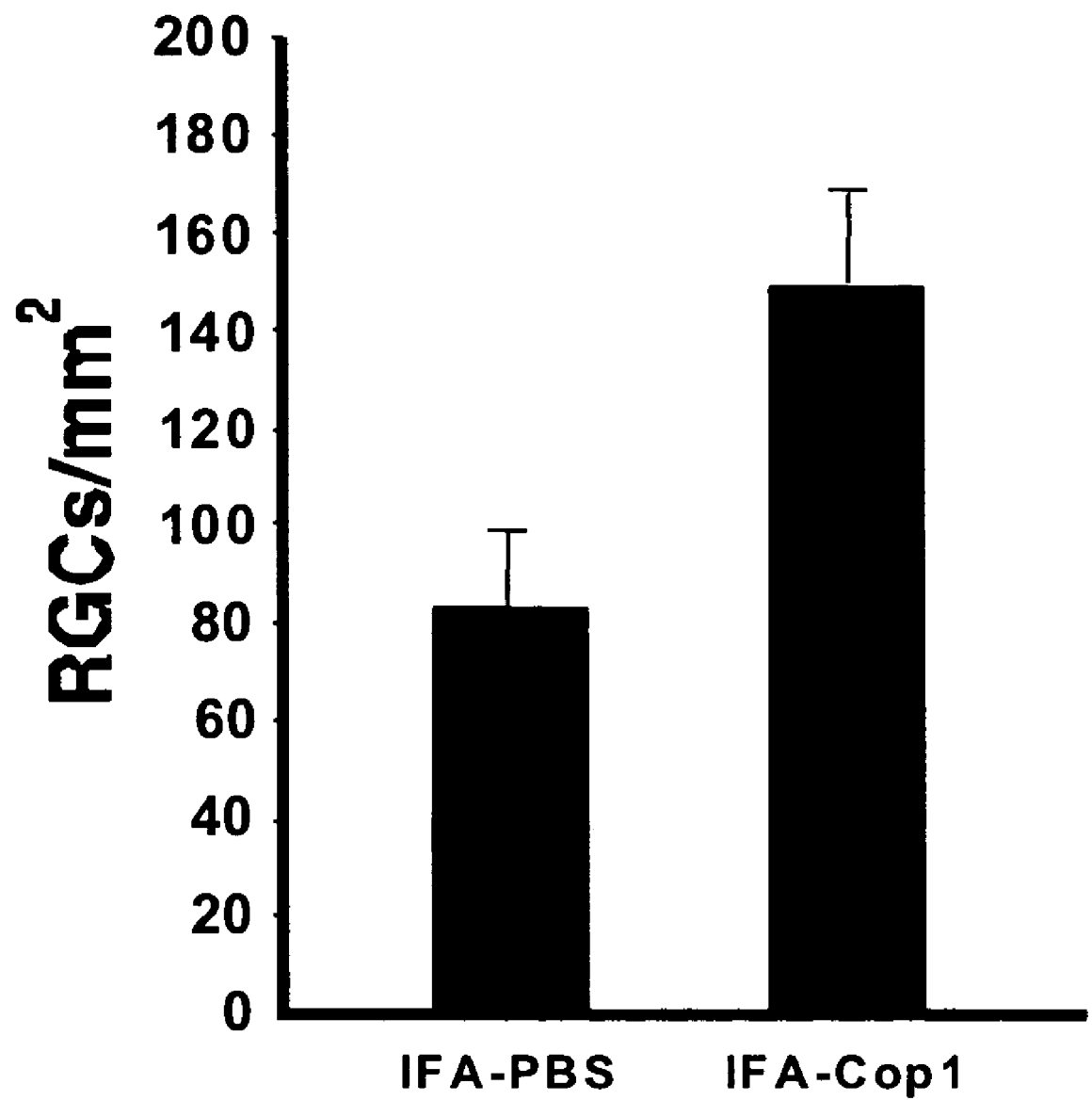
FIG. 3 is a graph showing how immunization with Cop 1 protects optic nerve fibers from secondary degeneration. Immediately after mild optic nerve injury, rats were immunized subcutaneously with PBS in IFA or Cop 1 in IFA. For assessment of secondary degeneration, the neurotracer dye 4-Di-10-Asp was applied to the optic nerve distal to the site of injury two weeks after crush injury. Five days later the rats were killed, and their retinas were excised and flat-mounted. Labeled (surviving) RGCs, from four fields located at approximately the same distance from the optic disk in each retina, were counted under the fluorescence microscope. The neuroprotective effect of Cop 1 immunization compared with that of PBS injection was signficant ($P<0.05$, Student's t-test). The results are the summary of two experiments. Each group contained eight to ten rats.

This example is intended to show that vaccination with Cop 1 in IFA, with a booster given two days later, results in an immune response strong enough for neuroprotection within the critical time window. Anesthetized rats were subjected to mild crush injury of the optic nerve, immediately vaccinated with Cop 1 in IFA, and a booster was given two days later. After two weeks the RGCs were retrogradely labeled, and five days later the rats were killed and their retinas excised. Rats vaccinated with Cop 1 in IFA showed evidence of significant neuroprotection compared to that in control rats injected with PBS in IFA (FIG. 3).

Example 3

Protection from Glutamate Toxicity

Experiment 1: Vaccination with Cop 1 Protects Optic Nerve Fibers from Glutamate Toxicity Because of the promising neuroprotection of injured nerves obtained by immunization with Cop 1, it is important to find out whether the protection would be restricted to nerve damage caused by trauma, or would be more general neuroprotection from hostile environmental conditions caused by glutamate-induced toxicity. Accordingly, the following experiment was conducted.

Immunization. C57Bl/6J OLA mice (8-10 weeks old) were each injected with a total of 75 μg of Cop 1 emulsified with an equal volume of complete Freund's adjuvant (CFA) containing 5 mg/ml of mycobacteria H37 RA (Difco). Mice in a second group were injected with an emulsion of phosphate-buffered saline (PBS) with CFA. The emulsion, in a total volume of 0.1 ml, was injected intradermally ten days before glutamate was introduced into the retina.

Glutamate Toxicity. Ten days after immunization, the mice were anesthetized, and 1 μl of saline containing 200 nmoles of glutamate was injected into the vitreous of the right eye. The left eye was not injected and served as a control.

Labeling of Retinal Ganglion Cells. Three days (72 hours) prior to assessment of RGC survival, each mouse was anesthetized and placed in a stereotactic device. The skull was exposed and kept dry and clean. The bregma was identified and marked. The designated point of injection was at a depth of 2 mm from the brain surface, 2.92 mm behind the bregma in the anteroposterior axis, and 0.5 mm lateral to the midline. A window was drilled in the scalp above the designated coordinates in the right and left hemispheres. The neurotracer dye FluoroGold (4% solution in saline; Fluorochrome, Dever, Colo.) was then applied (1 μl, at a rate of 0.5 μl/min) using a Hamilton syringe.

Figure 4:
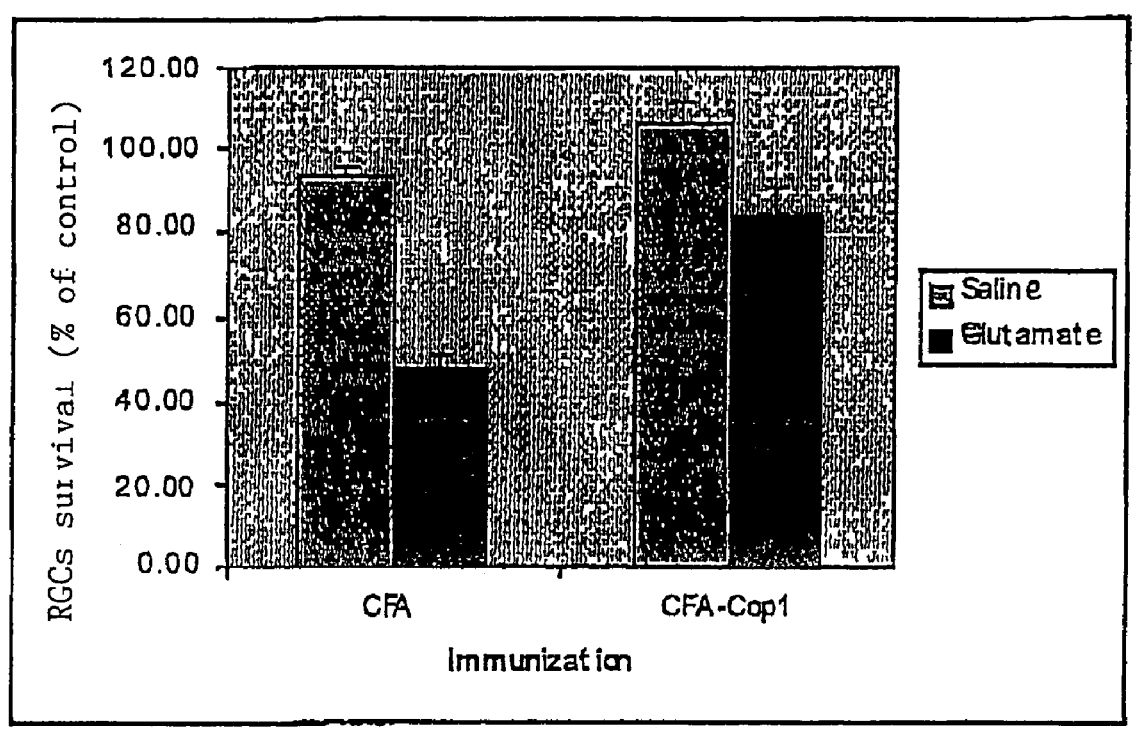
FIG. 4 is a graph showing how immunization with Cop 1 protects optic nerve fibers from glutamate toxicity. Mice were immunized with Cop 1 emulsified in complete Freund's adjuvant (CFA) and control mice were injected with CFA alone. One eye of each mouse was then injected with saline alone and the other with saline containing 200 nmoles of glutamate. Seven days after glutamate administration, the retinas were excised and flat-mounted. Labeled (surviving) retinal ganglion cells (RGCs) were counted. The bars shows the RGCs remaining as a percent of control for the CFA-treated mice receivinig either saline or saline with glutamate, and the CFA-Cop 1-treated mice receiving either saline or saline with Cop 1.

Assessment of RGC Survival. Seven days after glutamate administration the eyes were enucleated and their retinas were detached and prepared as flattened whole mounts in 4% paraformaldehyde solution. Labeled cells from six to eight fields of identical size (0.078 mm$^2$), located approximately 1 mm from the optic disk were counted under the fluorescence microscope and averaged. The results are shown in FIG. 4. Glutamate toxicity was found to be about four times higher in controls than in mice immunized with Cop 1.

Experiment 2: Vaccination for Protection of Neurons against Glutamate Toxicity and Ocular Hypertension In this study, active or passive immunization with a peptide derived from myelin oligodendrocyte glycoprotein (MMOG) or with MBP, which provides effective neuroprotection after axonal injury (Moalem et al, 1999a; Moalem et al, 1999b and Fisher et al, 2000), is shown not to protect the neurons from the toxicity caused by glutamate. Protection from glutamate toxicity was achieved, however, by vaccination with Cop-1. Immunization with Cop-1 was further shown to provide highly effective protection from retinal ganglion cell death induced by ocular hypertension in the rat model of glaucoma, under conditions where the pressure remains high and is not affected by the immunization.

Materials and Methods

Animals. All animals were handled according to the regulations formulated by the Institutional Animal Care and Use Committee. Mice of the C57BL/6J, and Balb/c strains, aged 8-13 weeks, and inbred adult Lewis rats aged 8-12 weeks were supplied by the Animal Breeding Center of the Weizmann Institute of Science and housed in light- and temperature-controlled rooms. The rats were matched for age and size in each experiment. Prior to their use in experiments, animals were anesthetized by intraperitoneal administration of ketamine 80 mg/kg and xylazine 16 mg/kg.

Antigens. Cop-1 was purchased from Teva Pharmaceuticals (Petah Tikva, Israel). Myelin oligodendrocyte glycoprotein (MOG) peptide (pMOG) 1-22 (GQFRVIGPGHPI-RALVGDEAEL) (SEQ ID NO:33) was synthesized in the laboratory of Prof. M. Fridkin at the Department of Chemistry of the Weizmann Institute of Science, using the Fmoc technique with an automatic multiple peptide synthesizer (AMS422, Abimed, Langenfeld, Germany). MBP from the spinal cords of guinea pigs was purchased from Sigma (Israel).

Immunization. Mice or rats were immunized with 75 μg or 100 μg of Cop-1, respectively, or 300 μg pMOG emulsified with an equal volume of complete Freund's adjuvant (CFA) containing 0.5 or 5 mg/ml *Mycobacterium tuberculosis*. The emulsion (total volume 0.15 ml) was injected subcutaneously at 1 site in the flank. One week later, the mice immunized with pMOG were given an identical immunization in the other flank as a booster. Control mice were injected with phosphate-buffered saline (PBS) in CFA (Difco, Detroit, Mich., USA).

Crush injury of the optic nerve. Mice or rats were anesthetized and subjected to severe crush injury in the intraorbital portion of the optic nerve, 1-2 mm from the eyeball. With the aid of a binocular operating microscope, the conjunctiva was incised and the optic nerve exposed. Using cross-action calibrated forceps and taking special care not to interfere with the blood supply, the nerve was crushed for 2 s (mice) or 30 s (rats).

Glutamate and NMDA Injections. The right eye of the anesthetized mouse or rat was punctured with a 27-gauge needle in the upper part of the sclera, and a 10-µl Hamilton syringe with a 30-gauge needle was inserted as far as the vitreal body. Mice were injected with a total volume of 1 µl (200 nmole) of L-glutamate or 1 µl of N-methyl-D-aspartate (NMDA; 75 nmole; RBI, Boston, Mass.) dissolved in saline. Rats were injected with 2 µl (375 nmole) of L-glutamate.

Pre-Injury Application Of Stereotactic Dye in Mice. The skull was exposed and kept dry and clean using 15% hydrogen peroxide. The bregma was identified and marked. A hole was drilled above the superior colliculus of each hemisphere (0.292 mm behind and 0.05 mm lateral to the midline). Using a stereotactic measuring device and a Hamilton injector, the mice were injected with FluoroGold (5% in saline, Fluorochrome, Denver, Colo.; 1 µl) at 1 point in the superior colliculus of each hemisphere, at a depth of 0.16 mm or 0.175 mm (depending on the mouse strain) from the bony surface of the brain. After completion of the injection, the wound was sutured. Retrograde uptake of the dye provides a marker of the living cells.

Assessment of Retinal Ganglion Cell Survival in Mice. Mice were given a lethal dose of pentobarbitone (170 mg/kg). Their eyes were enucleated and the retinas were detached and prepared as flattened whole mounts in paraformaldehyde (4% in PBS). Labeled cells from 4-6 selected fields of identical size (0.7 mm$^2$) were counted. The selected fields were located at approximately the same distance from the optic disk (0.3 mm) to overcome the variation in RGC density as a function of distance from the optic disk. Fields were counted under the fluorescence microscope (magnification ×800) by observers blinded to the treatment received by the mouse. The average number of RGCs per field in each retina was calculated.

Assessment of Retinal Ganglion Cell Survival in Rats. Survival of RGCs in rats was measured after post-injury application of the fluorescent lipophilic dye, 4-(4-(didecylamino)styryl)-N-methylpyridinium iodide (4-Di-10-Asp) (Molecular Probes Europe BV, Netherlands), distally to the optic nerve head. Labeling and measurement were carried out as follows: the optic nerve was exposed without damaging the retinal blood supply. Complete axotomy was performed 1-2 mm from the optic nerve head and solid crystals (0.2-0.4 mm diameter) of 4-Di-10-Asp were deposited at the site of the formed axotomy. Five days after dye application the rats were killed. The retina was detached from the eye, prepared as a flattened whole mount in 4% paraformaldehyde solution, and examined for labeled RGCs by fluorescence microscopy. In the IOP experimental animals, the ganglion cells were labeled by retrograde transport dextran tetramethylrhodamine (DTMR) (Molecular Probes, Oreg.). Crystals of 3000 MW DTMR were applied to the cut end of the optic nerve about 2 to 3 mm from the globe. Twenty-four hours later the retinas were whole-mounted and labeled ganglion cells in 8 regions, 2 in each quadrant, (0.66 to 1.103 mm from the edge of the optic disk) were counted with 400× magnification.

Generation of a Mouse Cop-1-T-Cell Line. A mouse T-cell line was generated from draining lymph node cells obtained from C57BL/6J mice immunized with Cop-1 antigen. The antigen was dissolved in PBS (1 mg/ml) and emulsified with an equal volume of CFA supplemented with 5 mg/ml *Mycobacterium tuberculosis* (Difco). Ten days after the immunization into the hind footpads, the mice were killed and their draining lymph nodes were surgically removed and dissociated. The cells were washed and activated with the antigen (10 µg/ml) in stimulation medium containing RPMI supplemented with L-glutamine (2 mM), 2-mercaptoethanol (5×10$^{-5}$ M), penicillin (100 units/ml), streptomycin (100 µg/ml), and autologous serum 0.5% (vol/vol). After incubation for 72 h at 37° C., 98% relative humidity and 10% $CO_2$, the cells were transferred to propagation medium consisting of RPMI supplemented with non-essential amino acids (1 ml/100 ml), sodium pyruvate (1 mM), L-glutamine, β-mercaptoethanol, penicillin and streptomycin, in the same concentrations as above, with the addition of 5% fetal calf serum (vol/vol) and 10% T-cell growth factor derived from the supernatant of concanavalin A-stimulated spleen cells. Cells were grown in propagation medium for 10-14 days before being restimulated with their antigen (10 µg/ml) in the presence of irradiated (2500 rad) spleen cells (10$^7$ cells/ml), in stimulation medium. The T-cell line was expanded by repeated stimulation and propagation. Basically the line has a similar phenotype to that previously described (Aharoni et al, 1997).

Generation of a Rat Cop-1-T-Cell Line. T cell lines were generated from draining lymph node cells obtained from Lewis rats immunized with the above antigens. The antigen was dissolved in phosphate-buffered saline (PBS) (1 mg/ml) and emulsified with an equal volume of incomplete Freund's adjuvant (IFA) (Difco Laboratories, Detroit, Mich.) supplemented with 4 mg/ml *Mycobacterium tuberculosis* (Difco). Ten days after the antigen was injected into the rats' hind footpads in 0.1 ml of the emulsion, the rats were killed and their draining lymph nodes were surgically removed and dissociated. The cells were washed and activated with the antigen (10 µg/ml) in stimulation medium containing Dulbecco's modified Eagle's medium (DMEM) supplemented with L-glutamine (2 mM), 2-mercaptoethanol (5×10$^{-5}$ M), sodium pyruvate (1 mM), penicillin (100 IU/ml), streptomycin (100 µg/ml), non-essential amino acids (1 ml/100 ml), and autologous serum 1% (volume/volume). After incubation for 72 h at 37° C., 98% relative humidity and 10% $CO_2$, the cells were transferred to propagation medium consisting of DMEM, L-glutamine, 2-mercaptoethanol, sodium pyruvate, non-essential amino acids, and antibiotics in the same concentrations as above, with the addition of 10% fetal calf serum (FCS) (volume/volume) and 10% T-cell growth factor derived from the supernatant of concanavalin A (ConA)-stimulated spleen cells. Cells were grown in propagation medium for 4-10 days before being restimulated with their antigen (10 µg/ml) in the presence of irradiated (2000 rad) thymus cells (10$^7$ cells/ml) in stimulation medium. The T cell lines were expanded by repeated stimulation and propagation.

Histological Analysis. Seven days after glutamate or saline injection the mice were killed by injection of a lethal dose of pentobarbitone (170 mg/kg) and their eyes were removed and fixed in formaldehyde (4% in PBS) for 48 h at 4° C. Sections (10 µm thick) were embedded in paraffin and stained with hematoxylin and eosin (H&E).

Generation of Ocular Hypertension in Rats/Elevation of Intraocular Pressure in Rats. Male Lewis rats were anesthetized with a mixture of ketamine (15 mg/kg), acepromazine (1.5 mg/kg), and xylazine (0.3 mg/kg). An increase in intraocular pressure (IOP) was achieved by laser photocoagulation of the limbal and episcleral veins. Rats received 2 laser treatments, 1 week apart, with a blue-green argon laser (1 watt for 0.2 s, delivering a total of 130-150 spots of 50 µm in the 2 treatments; Coherent, Palo Alto, Calif.). IOP was measured once a week using TONO-PEN (Mentor, Norwell, Mass.), after injecting the rats intramuscularly with the veterinary tranquilizer acepromazine 3.0 mg/kg and applying proparacaine 0.5% topically on the eyes to anesthetize the cornea.

Results

Myelin-Associated Antigens Are Not Protective against Glutamate Toxicity. The laboratory of the present inventor have previously demonstrated that passive and active immunization with myelin-associated antigens can reduce the post-traumatic degeneration associated with optic nerve crush injury in mice and rats (Examples 1 and 2; Moalem et al, 1999 and Fisher et al, 2000) and with spinal cord contusive injury in adult rats (Hauben et al, 2000a and Hauben et al, 2000b). To determine whether such immune neuroprotection is exerted after a non-mechanical injury as well, it was first examined whether active immunization with myelin-associated antigens or passive transfer of T cells reactive to these antigens provides neuroprotection against toxicity induced by intravitreal injection of glutamate. The optic nerves of rats and mice were subjected to crush injury. Using established protocols for immune neuroprotection from the laboratory of the present inventors, active immunization with MOG-derived peptides (Fisher et al, 2000) was performed in mice and passive transfer of anti-MBP T cells in rats (Moalem et al, 1999). Glutamate insult was inflicted by intravitreal injection of glutamate at a concentration previously shown to lead to RGC death that is measurable after 1 week in both mice and rats (Yoles et al, 2000).

Figure 5A:
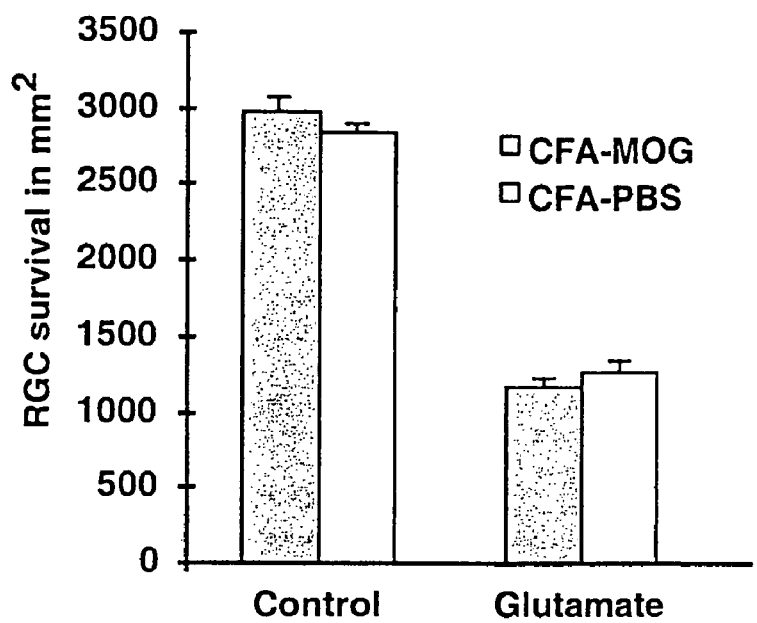
FIGS. 5A and 5B show immunization with pMOG (FIG. 5A) or passive transfer of anti-MBP T cells (FIG. 5B) does not protect mouse RGCs from glutamate toxicity.
Figure 5B:
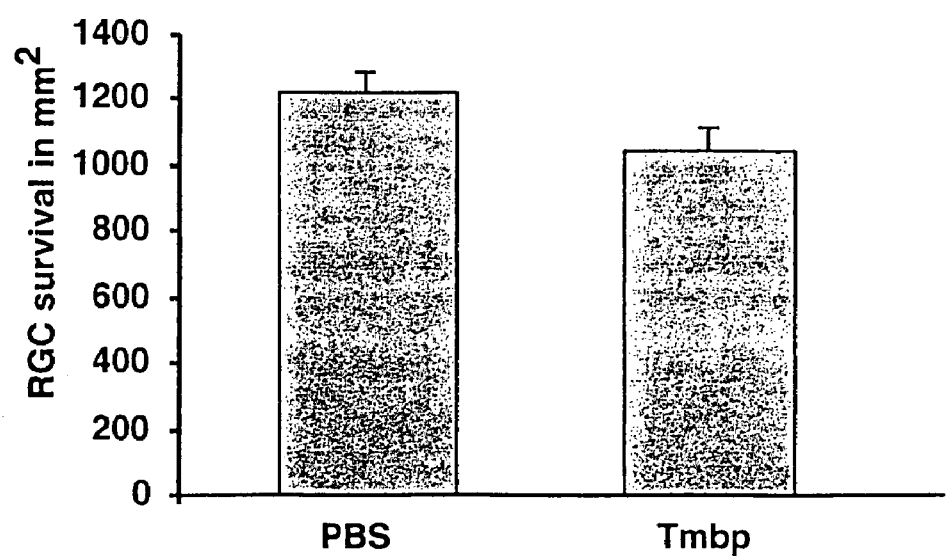

Mice were immunized with pMOG prior to the intravitreal injection of glutamate (200 nmole). When the RGC survival rate was assessed 1 week after glutamate injection, no evidence of a beneficial effect of the immunization with pMOG could be detected (FIG. 5A). Similarly, no beneficial effect was detectable when the glutamate injection was immediately followed by passive transfer of anti-MBP T cells in rats (FIG. 5B). Thus, although vaccination with pMOG(1-22) was recently shown to induce a neuroprotective response in mice after crush injury of the optic nerve (Fisher et al, 2000), no such neuroprotection was seen in the present study after the pMOG-vaccinated mice were subjected to glutamate insult.

These findings led the present inventors to consider 2 possibilities: either the loss of RGCs following glutamate toxicity is not amenable to immune neuroprotection, implying that glutamate-induced RGC death does not involve the immune system, or myelin-associated antigens such as pMOG and MBP are not the right antigens for protection against glutamate toxicity. Recent results from the laboratory of the present inventors (Kipnis et al, 2000), showing that the rate of cell death caused by glutamate is higher in rats or mice that lack mature T cells than in normal animals, strongly suggest that the beneficial physiological response to CNS insult involves T cells. Accordingly, boosting of this endogenous glutamate-induced T-cell response is likely to have a beneficial effect on the injured retina.

Figure 6A:
FIGS. 6A and 6B show the invasion of lymphocytes following intravitreal injection of glutamate. Glutamate was injected intravitreally into C57bl/6 mice. After 24 h, the eye was removed and processed for histology. H&E-stained retinal sections (10 μm thick) of both glutamate-injected (FIG. 6A) and control mice (FIG. 6B) are shown. Bar=200 μm.
Figure 6B:
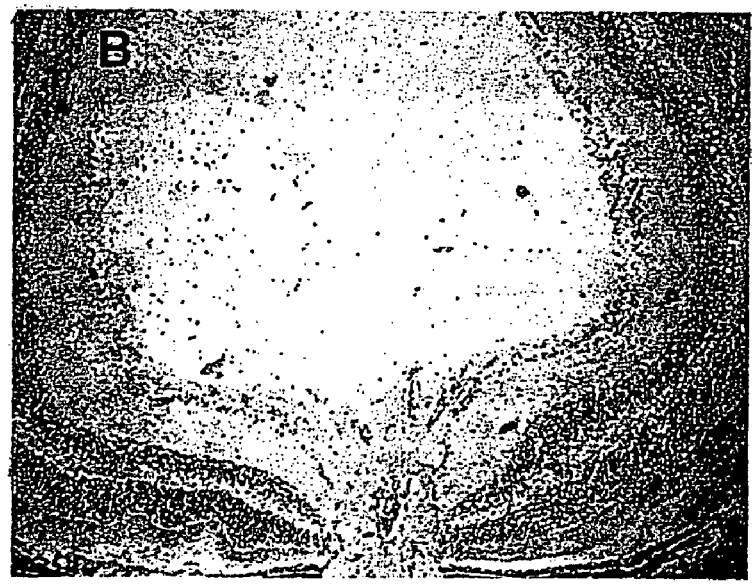

Cop-1 Immunization Protects against Glutamate Toxicity. While the search for a physiological antigen that might evoke a beneficial immune response to glutamate-induced toxicity is still a prime objective at this stage, the present inventors were interested in finding an antigen that might be used for purposes of exogenous immune system manipulation of the immune response to glutamate. First whether or not glutamate injection causes the RGCs to become accessible to lymphocytes was examined. It was found that large numbers of lymphocytes invade the glutamate-injected eye within 24 h of the glutamate injection (FIGS. 6A and 6B), suggesting that immune manipulation might influence the survival of RGCs following their local exposure to glutamate. Taken together, these two observations led the present inventors to believe that glutamate toxicity activates a T-cell mediated protective effect, and encouraged the present inventors to search for a way to boost this beneficial immune response. In seeking an appropriate antigen, the synthetic polymer Copolymer-1 (Cop-1), which is an oligopeptide used as a drug in patients with multiple sclerosis, and recently shown to boost neuroprotection in a model of optic nerve crush injury of the adult rat (Kipnis et al, 2000a), was considered a likely candidate.

Figure 7:
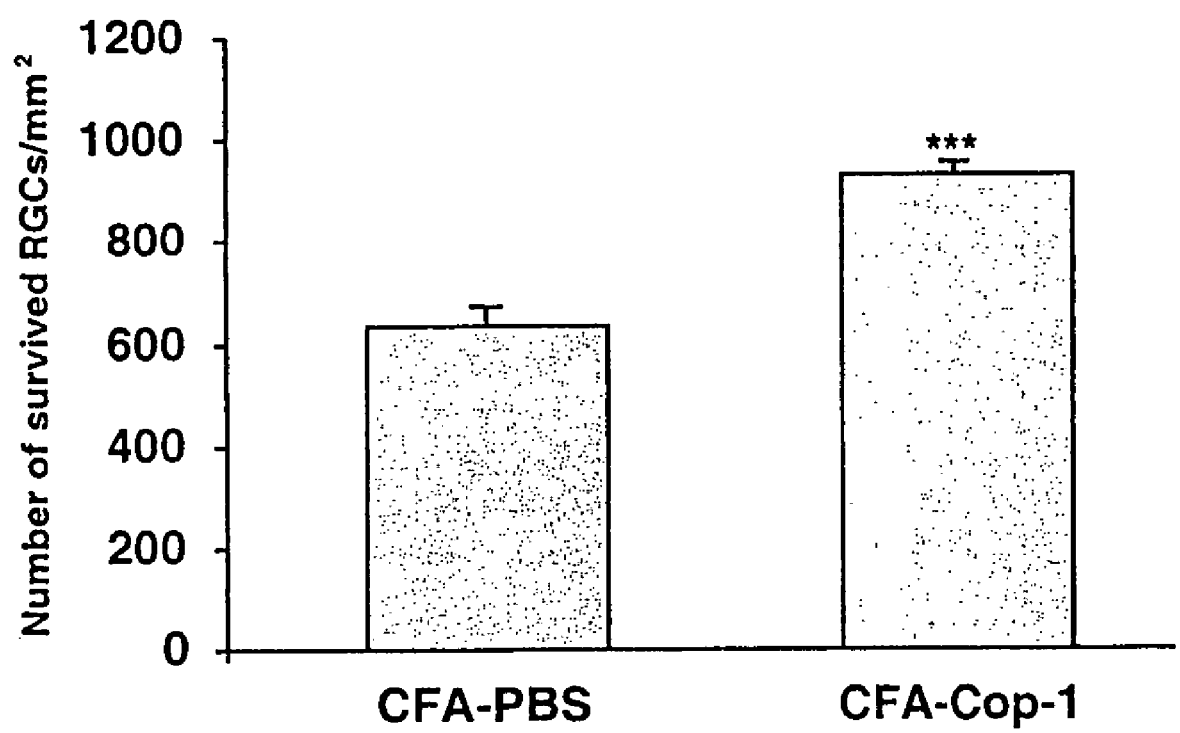
FIG. 7 shows the survival rate of retinal ganglion cells after optic nerve injury. The RGCs of inbred adult Balb/c were retrogradely labeled with FluoroGold (see Methods section of Example 3, Experiment 2) 10 days after being immunized with 50 μg of Cop-1 emulsified in CFA. Control mice were injected with PBS in CFA (n=8–12 in each group). Three days after labeling of RGCs, mice were subjected to a severe crush injury of the intraorbital portion of the optic nerve. Two weeks after injury, the retinas were excised and their labeled RGCs were counted (see Methods section of Example 3, Experiment 2). Relative to non-immunized controls, survival rates were significantly higher ($p<0.001$, Student's t test) in mice immunized with Cop-1 in CFA.

First, whether or not immunization with Cop-1 has a beneficial effect on RGC survival after optic crush injury in mice, and not only rats, was examined. For this study, Balb/c mice were used. Immunization with Cop-1, using a protocol that was found to be beneficial after optic nerve crush injury in rats, was also beneficial after optic nerve injury in mice (FIG. 7).

Figure 8A:
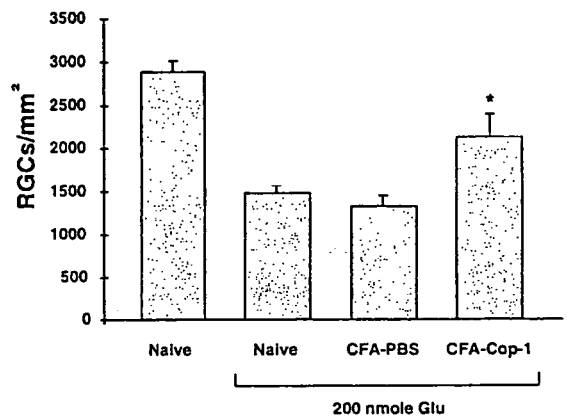
FIGS. 8A-8D show neuroprotection from glutamate toxicity by active immunization with Cop-1.
Figure 8B:
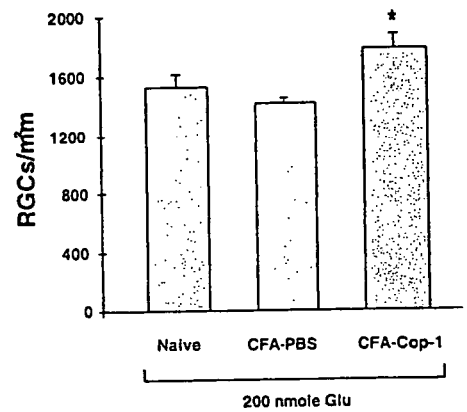
Figure 8C:
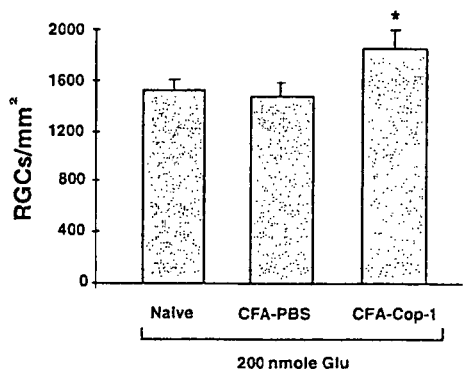
Figure 8D:
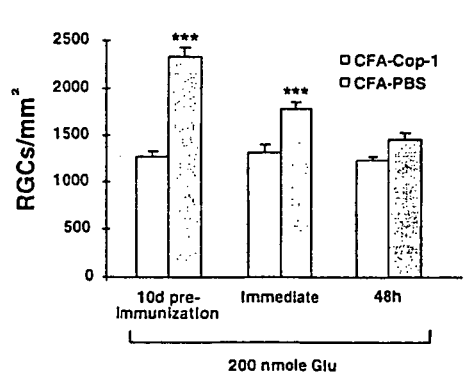
Figure 9:
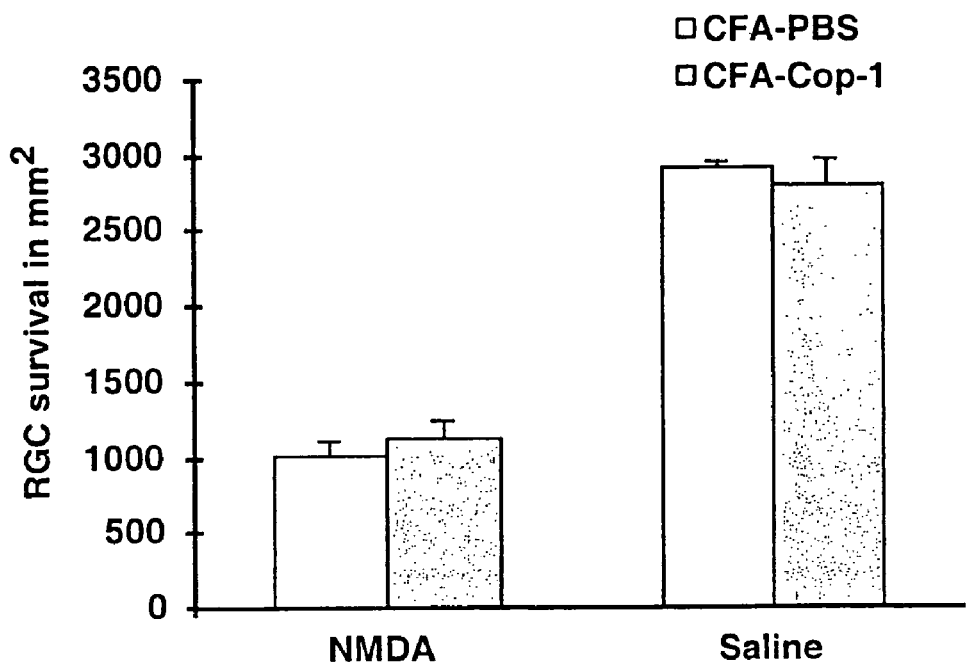
FIG. 9 shows Cop-1 immunization fails to protect mice from NMDA toxicity. Ten days before injection of NMDA (75 nmole), mice (n=5-7) were immunized by subcutaneous injection of Cop-1 in CFA or with PBS in CFA. Labeling of RGCs and counting of viable RGCs under fluorescence microscopy were as described for FIG. 5A. RGC survival in the Cop-1-immunized mice, expressed as a percentage of survival in a normal eye, was similar to that in the PBS-injected mice (p=0.55, Student's t test), indicating that no neuroprotection was obtained.

Next, whether or not the same protocol can lead to neuroprotection against glutamate-induced toxicity was investigated. For this study, C57bl/6 mice, in which the loss of retinal ganglion following glutamate insult is higher than in Balb/c (Kipnis et al, 2000b), was used. Ten days before intravitreal injection of glutamate, C57bl/6 mice were immunized with Cop-1 emulsified in adjuvant containing 5 mg/ml bacteria. This strain was selected in view of the recent finding in the laboratory of the present inventors that the loss of RGCs induced by glutamate injection in these mice is greater than in Balb/c mice because of a genetic linkage between neuronal loss and resistance to autoimmune disease (Kipnis et al, 2000b). Immunization with Cop-1 resulted in a significant reduction in glutamate toxicity (FIG. 8A). In an attempt to establish the therapeutic window for immunization with Cop-1 in this model, the experiment using Cop-1 emulsified in adjuvant containing 2 different concentrations of bacteria (0.5 or 5 mg/ml) was repeated and mice were immunized at different times in relation to the glutamate insult. Mice immunized on the day of glutamate injection still showed significantly higher rates of RGC survival than those seen in mice injected with PBS emulsified in the corresponding adjuvant (FIGS. 8B and 8C). Both adjuvants yielded significant effects. The protective efficacy of Cop-1 diminished with the time between immunization and glutamate insult: the mean percentage survival rate of RGCs when Cop-1 immunization was given immediately or 24 h after glutamate injection was significantly higher than in the PBS-injected retinas and was not significant when Cop-1 was given 48 h after glutamate injection (FIG. 8D). Interestingly, Cop-1 immunization failed to protect the mice from toxicity caused by NMDA (FIG. 9), recently shown by the laboratory of the present inventors to cause, in this in vivo model, RGC death with different features from those typical of apoptotic death.

Figure 10:
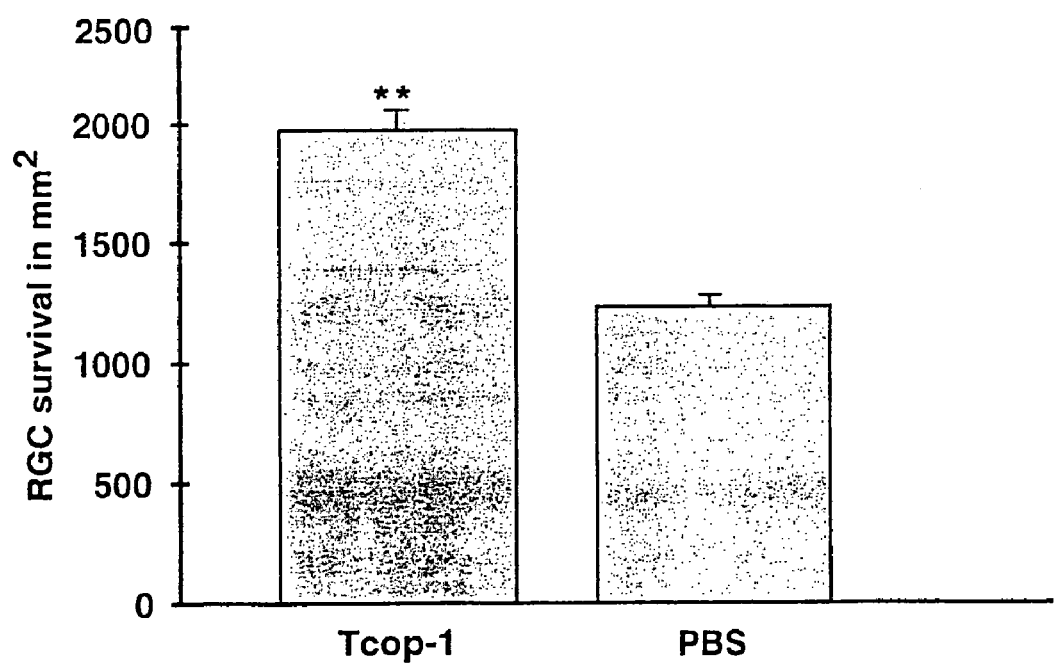
FIG. 10 shows Cop-1-reactive T cells protect RGCs from glutamate toxicity. Immediately after injection of glutamate (200 nmole), mice were injected with Cop-1-reactive T cells or with PBS. Dye application, preparation and counting of RGCs, and calculation of RGC survival were as described for FIG. 5B. Significantly more labeled RGCs are seen in the retinas of mice injected with Cop-1-reactive T cells than in the retinas of PBS-injected control mice (p<0.0007, Student's t test).

Adoptive Transfer of T Cells Reactive to Cop-1 Protects against Glutamate Toxicity. To determine whether the observed immunization with Cop-1 leads to T-cell-mediated neuroprotection against glutamate toxicity, $5 \times 10^6$ Cop-1-reactive T cells (250 µl intraperitoneally) were passively transferred into mice immediately after injection of glutamate (200 nmole). One week later, significantly more RGCs had survived in the mice injected with Cop-1-reactive T cells (1978±86, n=6) than in control mice (1238±2, n=3) injected intraperitoneally with PBS (FIG. 10).

Cop-1 Immunization Protects Retinal Ganglion Cells from Death Induced by Ocular Hypertension in Rats. Lewis rats were given 2 laser treatments, 1 week apart, to increase the IOP. Subsequent measurements at the indicated time points over a period of 3 weeks showed that by 2 weeks after the laser treatments the IOP had increased to 30±0.4 mm Hg (mean±SEM), and remained at approximately that level thereafter (FIG. 11A). The rate of retinal ganglion cell survival in these rats, measured 3 weeks after the initial laser treatment, was significantly lower (by 19.9%±0.51%, mean±SEM) than in non-lasered control rats (FIG. 11B). To examine the effect of Cop-1 immunization on the survival of retinal ganglion cells, rats were immunized with Cop-1 emulsified in CFA on the day of the first laser treatment. Control rats were injected with PBS in the same adjuvant. After 3 weeks, the retinal ganglion cells were retrogradely labeled, and 24 h later the retinas were excised, whole-mounted, and the labeled retinal ganglion cells were counted. The numbers of surviving retinal ganglion cells in the Cop-1-immunized rats were significantly higher than in the PBS/CFA-injected controls (FIG. 11C) the IOP in both groups of rats remained as high as that in a group of laser-treated rats that had received no injections (FIG. 11A). A similar though slightly smaller effect was seen in rats that were immunized with Cop-1 when their IOP was already high (FIG. 11D).

(7) Discussion of Results

No cure has yet been found for spinal cord lesions, one of the most common yet devastating traumatic injuries in industrial societies. It has been known for more than 40 years that CNS neurons, unlike neurons of the peripheral nervous system, possess only a limited ability to regenerate after injury. During the last two decades, attempts to promote regeneration have yielded approaches that lead to partial recovery. In the last few years it has become apparent that, although most of the traumatic injuries sustained by the human spinal cord are partial, the resulting functional loss is nevertheless far worse than could be accounted for by the severity of the initial insult; the self-propagating process of secondary degeneration appears to be decisive.

A substantial research effort has recently been directed to arresting injury-induced secondary degeneration. All attempts up to now have been pharmacologically based, and some have resulted in improved recovery from spinal shock. The present studies, in contrast, describe a cell therapy that augments what seems to be a natural mechanism of self-maintenance and leads, after a single treatment, to long-lasting recovery. The extent of this recovery appears to exceed that reported using pharmacological methods.

In most tissues, injury-induced damage triggers a cellular immune response that acts to protect the tissue and preserve its homeostasis. This response has been attributed to macrophages and other cells comprising the innate arm of the immune system. Lymphocytes, which are responsible for adaptive immunity, have not been thought to participate in tissue maintenance. Adaptive immunity, according to traditional teaching, is directed against foreign dangers. The present studies now show, however, that the adaptive T cell immune response can be protective even when there is no invasion by foreign pathogens. In the case of tissue maintenance, the specificity of the T cells is to tissue self-antigens.

The results of the above examples demonstrate the neuroprotective effect of T cells reactive to Cop 1 in a crush-injured CNS nerve, as well as in an optic nerve exposed to glutamate toxicity. In the rat model of partial optic nerve crush, adoptive administration of Cop 1-reactive T cells or vaccination with Cop 1 on the day of CNS injury had a marked preventive effect on the secondary degeneration of nerve fibers. This is the first time that vaccination is shown to be a possible method for preventing the spread of damage after traumatic injury to the optic nerve.

After crush injury of the rat optic nerve, injection of Cop 1-reactive T cells resulted in significant protection against the destructive effect of secondary degeneration. T cells accumulated at the site of injury, as expected, but they also accumulated in the non-injured nerve. Accumulation of T cells in the non-injured CNS is possible only if there is recognition of the T cell receptor by the presented antigen. Activated T cells can pass through the blood-brain barrier (BBB) regardless of their specificity, but only those that are reactive to CNS antigens can accumulate in the non-injured nerve (Hickey, 1991). Thus, the present findings demonstrate, for the first time, in vivo cross-recognition between Cop 1-reactive T cells and components of CNS myelin. This recognition at the injury site probably serves as the trigger for T cell activation, leading to the switching of T cells towards the protective phenotype, possibly via the secretion of suitable neurotrophic factors or other, yet to be discovered, factors by the activated T cells. This study demonstrates that Cop 1-reactive T cells activated by their specific antigen secrete significant amounts of BDNF, a neurotrophin that plays a major role in neuron survival (Yan et al, 1992; Sendtner et al, 1992).

Cop-1 was originally designed to mimic the activity of myelin basic protein (MBP) and to induce the inflammatory demyelinating disease EAE in rodents. It was found, however, to be non-encephalitogenic and even to suppress EAE induced by MBP (Teitelbaum et al, 1971), proteolipid protein (PLP) (Teitelbaum et al, 1996), or MOG (Ben-Nun et al, 1996). Cop-1 prevents the development of EAE in rodents and ameliorates multiple sclerosis in humans. Studies have demonstrated partial cross-reactivity between antibody to Cop-1 and MBP or between T cells directed to these antigens (Webb et al, 1973 and Teitelbaum et al, 1988). Cop-1 can serve as an antagonist of the T-cell antigen receptor for the immunodominant MBP epitope (Aharoni et al, 1998). It can also bind to various major histocompatibility complex (MHC) class II molecules and prevent them from binding to T cells with specific antigen-recognition properties (Fridkis-Hareli et al, 1998). In rodents, Cop-1 induces the expression of regulatory cells that suppress the encephalitogenic T cells. Adoptive transfer of such T cells in rodents was found to prevent the development of EAE induced by MBP (Aharoni et al, 1993), PLP (Teitelbaum et al, 1996), or whole spinal cord homogenate (Aharoni et al, 1997).

Thus, immunization with Cop 1, unlike immunization with MBP and other myelin-associated proteins, does not induce EAE, and the T cells evoked by Cop 1, in the absence of adjuvants, are of a regulatory nature. Immunization with Cop 1 in IFA immediately after the injury, followed by a booster 2 days later, had a strongly neuroprotective effect. Such immunization is likely to reach the peak of its cellular response within about a week, but it is reasonable to assume that even before that time the number of T cells present in the CNS will be apparently large enough to exert at least some neuroprotective activity. It is known that following immunization with MBP, symptoms of EAE appear 10 days later, indicating that by that time the immune response is strong enough for encephalitogenic T cells to accumulate at the site of injury, inflict their damage, and produce EAE symptoms. The present study suggests that, after immunization with Cop 1 in IFA followed two days later by a booster, the immune response at the optic nerve was sufficient to prevent secondary degeneration. It is possible that this response was somewhat delayed relative to the response obtained after passive transfer of T cells, but it was nevertheless still achieved within the time window needed for protection of nerve fibers that escaped the primary lesion. Previous studies in the rat optic nerve have shown that the loss of neurons resulting from secondary degeneration is about 25% a week after mild crush injury and about 55% two weeks after the injury (Yoles, 1998). Thus, even if the response took one week to reach the required strength, there would still be nerve fibers in need of protection at that time. A comparison of the results obtained after adoptive transfer of activated Cop 1-reactive T cells and after active immunization with Cop 1 suggests that there is no significant difference between the two treatments in the time taken to become maximally effective, as the extent of protection from secondary degeneration was almost the same in both. It should be emphasized that Cop 1 is displaying here an effect that is opposite to its known effect; Cop 1 is known as an agent designed to suppress T-cell autoimmunity, whereas here it has an effect that requires activation of specific anti-myelin T-cell autoimmunity.

In conclusion, earlier studies have shown that axonal injury in the rat CNS awakens an autoimmune T cell response which is directed against myelin proteins, but is too weak to protect the nerve fibers from secondary degeneration. Boosting of this immune response without risk of accompanying autoimmune disease was achieved in this study by using a copolymer which is cross-recognized by the CNS but is not encephalitogenic. The T cell immune response to the polymer, obtained either by passive transfer or by immunization at the time of the injury, provides an effective means of post-traumatic maintenance. The T-cell-mediated neuroprotection demonstrated here is applicable to both chronic and acute injuries of CNS nerves, in which neurons are vulnerable to degeneration and amenable to neuroprotection. It is also applicable to protection from the primary and secondary degeneration caused by glutamate toxicity. T cell-dependent immune neuroprotection, achieved by passive or active immunization with Cop-1, is also shown here in the results to be an effective therapy for glutamate-induced toxicity in mice and in a rat model of chronically high IOP.

As the results of the studies in Example 3 show that both passive and active immunization with Cop-1 provide effective neuroprotection from glutamate toxicity, vaccination can be developed as a way to reduce the neuronal toxicity associated with glutamate. These observations have a number of interesting implications: (i) Cop-1, which is used as an immunosuppressive drug in patients with the autoimmune disease multiple sclerosis, is effective as a vaccination against glutamate-induced neurotoxicity; (ii) loss of CNS neurons due to a local stress signal can benefit from systemic immune manipulation; (iii) the same neurons, in this case the RCGs, can benefit from a systemic immune response regardless of the nature and site of the insult, though the antigenic specificity of the response may vary; (iv) the beneficial activity of Cop-1, although apparently not dependent on the type of insult (mechanical or biochemical), appears to be critically dependent on the mechanism of death that the insult activates. In Example 3, the induced immune activity protected the cells against death caused by glutamate but not against death caused by NMDA; (v) Cop-1, acting as an immunogen, may induce neuroprotection by a mechanism that does not necessarily require cross-recognition of myelin proteins.

It should be stressed that there is an important difference between immune neuroprotection against secondary degeneration and immune therapy for autoimmune diseases. While the former requires active involvement of beneficial T cells, the latter may benefit from either immune modulation of encephalitogenic T cells or from their suppression. Cop-1, acting as an immunogen, may serve both purposes neuroprotection from neuronal insult and therapy for autoimmune diseases. Presumably it achieves this by evoking a "safe" T cell response, which on the one hand provides the beneficial autoimmune T cell response needed for neuroprotection (Moalem et al, 1999a; Moalem et al, 1999b; Kipnis et al, 2000a; Moalem et al, 2000c; and Schwartz et al, 1999), and on the other hand the immune modulation required for avoidance of autoimmune disease (Neuhaus et al, 2000).

T cells reactive to MBP were shown in the laboratory of the present inventors to be neuroprotective in rat models of partially crushed optic nerves (Moalem et al, 1999 and Schwartz et al, 1999) and spinal cord contusive injury (Hauben et al, 2000a). The previous findings in the laboratory of the present inventors demonstrated in vivo cross-recognition between Cop-1-reactive T cells and components of CNS myelin (Kipnis et al, 2000a). The present inventors suggested that such recognition, by triggering T cell reactivation and thus causing the T cells to switch towards a protective phenotype, might represent a possible mechanism underlying T cell neuroprotection after axonal injury. It was further shown by the present inventors that Cop-1-reactive T cells (Examples 1 and 2; Kipnis et al, 2000a), like MBP-reactive T cells (Moalem et al, 2000), when activated by their specific antigen secrete significant amounts of brain-derived neurotrophic factor, a neurotrophin that plays a major role in neuronal survival (Sendtner et al, 1992 and Yan et al, 1992). In Example 1, the laboratory of the present inventors examined T-cell immunity to Cop-1 after physical trauma to the white matter, where anti-Cop-1 T cells can cross-react with exposed myelin epitopes. The present finding in Example 3 that immunization with Cop-1 is active against glutamate toxicity, which directly affects neuronal cell bodies under conditions where no myelin antigens are likely to be involved, may suggest that anti-Cop-1 T cells, due to their heterogeneity, respond to a variety of antigens including those associated with the retina. The Cop-1-reactive T cells may interact directly with glutamate itself. Such interaction could convert the Cop-1-reactive T cells, or endogenous T cells, to a protective phenotype.

The possibility that Cop-1-reactive T cells might interact with the injected glutamate within the vitreous or with microglia-activated cells within the retina is supported by the large numbers of invading lymphocytes observed in the vitreous 24 h after glutamate injection. In mice injected with Cop-1, the invading lymphocytes are likely to include some that are specific to Cop-1. This observation, together with the finding that passive transfer of Cop-1-reactive T cells has a similar effect to that of active immunization with Cop-1, suggests that the effect of the vaccination is indeed mediated by T cells, rather than by humoral immunity or by Cop-1 itself. Because glutamate, being a mediator of secondary degeneration, appears at some distance in time from the primary insult (Yoles et al, 1998), a treatment window of 24 h in the case of direct glutamate toxicity may imply that in cases of CNS trauma the window for treatment with Cop-1 is much wider. It is interesting to note that Cop-1 had no protective effect when the toxic insult was induced by NMDA. This is in line with studies from the laboratory of the present inventors showing that NMDA imposes an almost immediate death signal, without clear signs of apoptosis and with no apparent opportunity for therapy other than with NMDA-receptor antagonists. It is therefore not surprising that immunization with Cop-1 was ineffective against NMDA-induced toxicity. It remains to be established whether the activity of Cop-1 as a neuroprotective rather than as a suppressive agent is dependent on its route of administration. It also remains to be determined how the local accumulation of T cells specific to CNS antigens, or of T cells specific to cross-reactive antigens such as Cop-1, mediate neuroprotection after CNS insults.

The T-cell-mediated neuroprotection demonstrated in the studies in Example 3 might be applicable to both chronic and acute injuries of CNS nerves in which neurons are vulnerable to degeneration and amenable to neuroprotection (Schwartz et al, 2000a; Schwartz et al, 2000b; Doble et al, 1999; and Grunblatt et al, 2000). A chronic condition, glaucoma, is often associated with IOP, and is a leading cause of blindness. It is common experience, however, that the disease may continue to progress even though the IOP remains within the normal range, suggesting that mechanical compression is probably not the sole reason for optic nerve damage and that treatment, in addition to lowering the IOP, should therefore include neuroprotective therapy (for review see Osborne et al, 1999; Schwartz et al, 2000c; and Weinreb et al, 1999). Recent studies have shown, for example, that treatment with a glutamate antagonist (Chaudhary et al, 1998) or a nitric oxide synthase inhibitor (Neufeld et al, 1999) attenuates retinal ganglion cell death in a rat model of increased IOP. There is a danger, however, that interference with the physiological response by these agents, though possibly beneficial at the site of pathology, might be harmful for the normal tissue, leading to undesirable side effects. A more favorable approach from the clinical point of view, therefore, is to harness and augment the tissue's own defense machinery.

The present finding of neuroprotection achieved even when the pressure remains high is potentially of great advantage from the clinical point of view. This is because even a pressure reduced to normal is not necessarily safe for patients with glaucoma, in whom the remaining neurons are more vulnerable than normal ones (Agis, 2000). Moreover, reduction of the IOP to what might be considered safe in such patients, i.e., to 12 mm Hg, might not be feasible.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Agis, *Am J Ophthalmol* (2000)

Aharoni et al, "T suppressor hybridomas and interleukin-2-dependent lines induced by copolymer 1 or by spinal cord homogenate down-regulate experimental allergic encephalomyelitis", *Eur J Immunol* 23: 17-25 (1993)

Aharoni et al, "Copolymer 1 induces T cells of the T helper type 2 that crossreact with myelin basic protein and suppress experimental autoimmune encephalomyelitis", *Proc Natl Acad Sci USA* 94(20): 10821-10826 (1997)

Ashwood-Smith MJ, "Preservation of mouse bone marrow at −79 degrees C. with dimethyl sulphoxide", *Nature* 190: 1204-1205 (1961)

Bazan et al, "Mediators of injury in neurotrauma: intracellular signal transduction and gene expression", *J Neurotrauma* 12(5): 791-814 (1995)

Ben-Nun et al, "The rapid isolation of clonable antigen-specific T lymphocyte lines capable of mediating autoimmune encephalomyelitis", *Eur J Immunol* 11 (3): 195-199 (1981a)

Ben-Nun et al, "Vaccination against autoimmune encephalomyelitis with T-lymphocyte line cells reactive against myelin basic protein", *Nature* 292 (5818): 60-61 (1981b)

Ben-Nun et al, "Experimental autoimmune encephalomyelitis (EAE) mediated by T cell lines: process of selection of lines and characterization of the cells", *J Immunol* 129 (1): 303-308 (1982)

Ben-Nun et al, "The autoimmune reactivity to myelin oligodendrocyte glycoprotein (MOG) in multiple sclerosis is potentially pathogenic: effect of copolymer 1 on MOG-induced disease", *J Neurol* 243(4Supl): S14-22 (1996)

Bornstein et al, "Clinical trials of Cop 1 in multiple sclerosis", *Handbook of Multiple Sclerosis*, ed. Cook S.D. Marcel Dekker, Inc., p. 469 (1990)

Brauner-Osborne et al, "A new structural class of subtype-selective inhibitor of cloned excitatory amino acid transporter, EAAT2" *Eur J Pharmacol*, 406: 41-44 (2000)

Burns et al, "Isolation of myelin basic protein-reactive T-cell lines from normal human blood", *Cell Immunol* 81(2): 435-440 (1983)

Chaudhary et al, ""MK801-a neuroprotectant in rat hypertensive eyes", *Brain Res* 792(1): 154-158 (1998)

Doble, "The role of excitotoxicity in neurodegenerative disease: implications for therapy", *Pharmacol Ther* 81: 163-221

Dreyer et al, "Elevated glutamate levels in the vitreous body of humans and monkeys with glaucoma", *Arch Ophthalmol* 114: 299-305 (1996)

Duvdevani et al, *Restor Neurol Neurosci* 2: 31-38 (1990)

Faden et al, "Pharmacological strategies in CNS trauma", *Trends Pharmacol Sci* 13(1): 29-35 (1992)

Faden A I, "Experimental neurobiology of central nervous system trauma", *Crit Rev Neurobiol* 7(3-4): 175-186 (1993)

Fisher et al, *J Neurosci* (2000)

Fridkis-Hareli et al, "Direct binding of myelin basic protein and synthetic copolymer 1 to class II major histocompatibility complex molecules on living antigen-presenting cells-specificity and promiscuity", *Proc Natl Acad Sci USA* 91(11): 4872-4876 (1994).

Fridkis-Hareli et al, "Promiscuous binding of synthetic copolymer 1 to purified HLA-DR molecules", *J Immunol* 160(9): 4386-4397 (1998)

Fridkis-Hareli et al, "Binding of random copolymers of three amino acids to class II MHC molecules", *Int Immunol* 11(5): 635-641 (1999a)

Fridkis-Hareli et al, "Binding motifs of copolymer 1 to multiple sclerosis- and rheumatoid arthritis-associated HLA-DR molecules", *J Immunol* 162(8): 4697-4704 (1999b)

Gillis et al, "T cell growth factor: parameters of production and a quantitative microassay for activity", *J Immunol* 120: 2027-2032 (1978)

Gorin, N.C., "Collection, manipulation and freezing of haemopoietic stem cells", *Clin Haematol* 15(1): 19-48 (1986)

Grunblatt et al, "MPTP and 6-hydroxydopamine-induced neurodegeneration as models for Parkinson's disease: neuroprotective strategies", *J Neurol, Suppl* 2: 1195-1102 (2000)

Hauben et al, "Autoimmune T cells as potential neuroprotective therapy for spinal cord injury", *Lancet* 355: 286-287 (2000)

Hickey, W. F. et al, "T-lymphocyte entry into the central nervous system", *J Neurosci Res* 28(2): 254-260 (1991)

Hirschberg et al, "Accumulation of passively transferred primed T cells independently of their antigen specificity following central nervous system trauma" *J Neuroimmunol* 89(1-2): 88-96 (1998)

Hovda et al, "Diffuse prolonged depression of cerebral oxidative metabolism following concussive brain injury in the rat: a cytochrome oxidase histochemistry study", *Brain Res* 567(1): 1-10 (1991)

Hunig et al, "A monoclonal antibody to a constant determinant of the rat T cell antigen receptor that induces T cell activation. Differential reactivity with subsets of immature and mature T lymphocytes", *J Exp Med* 169: 73-86 (1989)

International Atomic Energy Agency, Bone-Marrow Conservation, Culture and Transplantation, Proceedings of a Panel, Moscow, Jul. 22-26, 1968, Vienna, pp. 107-186 (1969)

Johnson et al, "Cop 1 positive results-a phase III trial in relapsing remitting", MS. 11th Annual Meeting A.N.A. (1994)

Johnson et al, "Copolymer 1 reduces relapse rate and improves disability in relapsing-remitting multiple sclerosis: results of a phase III multicenter, double-blind placebo-controlled trial. The Copolymer 1 Multiple Sclerosis Study Group," *Neurology* 1: 65 (1995)

Kipnis et al, "T cell immunity to copolymer 1 confers neuroprotection on the damaged optic nerve: possible therapy for optic neuropathies", *Proc Natl Acad Sci USA,* 97: 7446-7451 (2000a)

Kipnis et al (2000b)

Kramer et al, "Gene transfer through the blood-nerve barrier: NGF-engineered neuritogenic T lymphocytes attenuate experimental autoimmune neuritis", *Nat Med* 1(11): 1162-1166 (1995)

Lazarov-Spiegler et al, "Transplantation of activated macrophages overcomes central nervous system regrowth failure", *FASEB J* 10(11): 1296-1302 (1996)

Lehman, K., "Acrylic Coatings in Controlled Realse Tablet Manufacturer", Manufacturing Chemist and Aerosol News, p. 39 (1973)

Lewis et al, "The effect of cooling regimens on the transplantation potential of marrow", *Transfusion* 7(1): 17-32 (1967)

Linner et al, "A new technique for removal of amorphous phase tissue water without ice crystal damage: a preparative method for ultrastructural analysis and immunoelectron microscopy", *J Histochem Cytochem* 34(9): 1123-1135 (1986)

Livesey and Linner, *Nature* 327: 255 (1987)

Lovelock J E, "The protective action of neutral solutes against haemolysis by freezing and thawing", *Biochem J* 56(2): 265-270 (1954)

Lovelock et al, "Prevention of freezing damage to living cells by dimethyl sulphoxide", *Nature* 183(4672): 1394-1395 (1959)

Lynch et al, "Secondary mechanisms in neuronal trauma, *Curr Opin Neurol* 7(6): 510-516 (1994)

Martin et al, "Fine specificity and HLA restriction of myelin basic protein-specific cytotoxic T cell lines from multiple sclerosis patients and healthy individuals", *J Immunol* 145 (2): 540-548 (1990)

Martin R, "Immunological aspects of experimental allergic encephalomyelitis and multiple sclerosis and their application for new therapeutic strategies", *J Neural Transm Suppl.* 49: 53-67 (1997)

Mazur P, "Cryobiology: the freezing of biological systems", *Science* 168(934): 939-949 (1970)

McIntosh T K, "Novel pharmacologic therapies in the treatment of experimental traumatic brain injury: a review", *J Neurotrauma* 10(3): 215-261 (1993)

Meldrum, "Glutamate as a neurotransmitter in the brain: review of physiology and pathology", *J Nutr* 130:(4S Suppl): 1007S-1015S (2000)

Moalem et al, "Autoimmune T cells protect neurons from secondary degeneration after central nervous system axotomy", *Nat Med* 5: 49-55 (1999a)

Moalem et al, "Differential T cell response in central and peripheral nerve injury: connection with immune privilege", *FASEB J,* 13: 1207-17 (1999b)

Moalem et al, "Production of neurotrophins by activated T cells: implications for neuroprotective autoimmunity", *J Autoimmun,* 15: 331-345 (2000)

Mor et al, "Clinical modeling of T cell vaccination against autoimmune diseases in rats. Selection of antigen-specific T cells using a mitogen", *Clin Invest* 85(5): 1594-1598 (1990)

Mor et al, "Pathogenicity of T cells responsive to diverse cryptic epitopes of myelin basic protein in the Lewis rat", *J Immunol* 155(7): 3693-3699 (1995)

Neufeld et al, "Inhibition of nitric-oxide synthase 2 by aminoguanidine provides neuroprotection of retinal ganglion cells in a rat model of chronic glaucoma", *Proc Natl Acad Sci USA,* 96(17): 9944-9948 (1999)

Neuhaus et al, "Multiple sclerosis: comparison of copolymer-1-reactive T cell lines from treated and untreated subjects reveals cytokine shift from T helper 1 to T helper 2 cells", *Proc Natl Acad Sci USA,* 97: 7452-7457 (2000)

Osborne et al, "The potential of neuroprotection in glaucoma treatment", *Curr Opin Ophthalmol,* 10(2): 82-92 (1999)

Ota et al, "T-cell recognition of an immunodominant myelin basic protein epitope in multiple sclerosis", *Nature* 346 (6280): 183-187 (1990)

Pette et al, "Myelin basic protein-specific T lymphocyte lines from MS patients and healthy individuals", *Proc Natl Acad Sci USA* 87(2): 7968-7972 (1990)

Phan The Tran et al, "Survival of mouse bone-marrow cells frozen and thawed in solutions of amino acids", *Exp Cell Res* 20: 651-654 (1960a)

Phan The Tran et al, "Protection of mouse bone marrow by inorganic compounds during freezing and thawing", *Proc Soc Exp Biol Med* 104: 388-390 (1960b)

Phan The Tran et al, in Radiobiology, Proceedings of the Third Australian Conference on Radiobiology, Ilbery, P. L. T., ed., Butterworth, London, p. 59 (1961)

Pitt et al, "Glutamate excitotoxicity in a model of multiple sclerosis", *Nat Med* 6: 67-70 (2000)

Rapalino et al, "Implantation of stimulated homologous macrophages results in partial recovery of paraplegic rats", *Nat Med* 4(7): 814-821 (1998)

Rapatz et al, "Preservation of erythrocytes in blood containing various cryoprotective agents, frozen at various rates and brought to a given final temperature", *Cryobiology* 5(1): 18-25 (1968)

Rinfret A P, "Factors affecting the erythrocyte during rapid freezing and thawing", *Ann N Y Acad Sci* 85: 576-594 (1960)

Rowe et al, *Fed Proc* 21: 157 (1962a)

Rowe and Rinfret, *Blood* 20: 636 (1962b)

Rowe A, "Biochemical aspects of cryoprotective agents in freezing and thawing", *Cryobiology* 3(1): 12-18 (1966)

Schluesener et al, "Autoaggressive T lymphocyte lines recognizing the encephalitogenic region of myelin basic protein: in vitro selection from unprimed rat T lymphocyte populations", *J Immunol* 135(5): 3128-3133 (1985)

Schoepp et al, "Pharmacological agents acting at subtypes of metabotropic glutamate receptors", *Neuropharmacology*, 38: 1431-1476 (1999)

Schwartz et al, "Innate and adaptive immune responses can be beneficial for CNS repair", *Trends Neurosci* 22: 295-299 (1999a)

Schwartz et al, "Neuroprotection: a new treatment modality for glaucoma?", *Curr Opin Ophthalmol* 11(2): 82-92 (1999b)

Schwartz et al, "Self-destructive and self-protective processes in the damaged optic nerve: implications for glaucoma", *Invest Ophthalmol Vis Sci*, 41(2): 349-351 (2000a)

Schwartz et al, "Neuroprotection: a new treatment modality for glaucoma?", *Curr Opin Ophthalmol* 11(2): 107-111 (2000b)

Sela et al, *Bull Inst Pasteur* (Paris) 88: 303-314 (1990)

Sendtner et al, "Brain-derived neurotrophic factor prevents the death of motoneurons in newborn rats after nerve section", *Nature* 360: 757-759 (1992)

Sloviter and Ravdin, *Nature* 196: 548 (1962)

Spitzer et al, "High-dose combination chemotherapy with autologous bone marrow transplantation in adult solid tumors", *Cancer* 45(12): 3075-3085, 1980

Streilein J W, "Immune privilege as the result of local tissue barriers and immunosuppressive microenvironments", *Curr Opin Immunol* 5(3): 428-423 (1993)

Streilein J W, "Unraveling immune privilege", *Science* 270 (5239): 1158-1159 (1995)

Suruhan-Direskeneli et al, "Human T cell autoimmunity against myelin basic protein: CD4+ cells recognizing epitopes of the T cell receptor beta chain from a myelin basic protein-specific T cell clone", *Eur J Immunol* 23(2): 530-536 (1993)

Teitelbaum et al, "Suppression of experimental allergic encephalomyelitis by a synthetic polypeptide" *Eur J Immunol* 1(4): 242-248 (1971)

Teitelbaum et al, "Suppression of experimental allergic encephalomyelitis in rhesus monkeys by a synthetic basic copolymer", *Clin Immunol Immunopathol* 3(2): 256-262 (1974a)

Teitelbaum et al, "Suppression of experimental allergic encephalomyelitis in baboons by Cop 1", *Israel J. Med. Sci* 13: 1038 (1974b)

Teitelbaum et al, "Specific inhibition of the T-cell response to myelin basic protein by the synthetic copolymer Cop 1", *Proc Natl Acad Sci USA* 85(24): 9724-9728 (1988)

Teitelbaum et al, "Copolymer 1 inhibits chronic relapsing experimental allergic encephalomyelitis induced by proteolipid protein (PLP) peptides in mice and interferes with PLP-specific T cell responses", *J Neuroimmunol* 64: 209-217 (1996)

Webb et al, "Correlation between strain differences in susceptibility to experimental allergic encephalomyelitis and the immune response to encephalitogenic protein in inbred guinea pigs", *Immunol Commun* 2(2): 185-192 (1973)

Weinreb et al, "Is neuroprotection a viable therapy for glaucoma?", *Arch Ophthalmol,* 117(11): 1540-1544 (1999)

Werkele H, in *The Blood-Brain Barrier*, Pardridge, Ed., Raven Press, Ltd. New York, pp. 67-85 (1993)

Wu, D. et al, *J Neurochem* 62: 37-44 (1994)

Yan et al, "Brain-derived neurotrophic factor rescues spinal motor neurons from axotomy-induced cell death", *Nature* 360: 753-755 (1992)

Yoles, et al, "GM1 reduces injury-induced metabolic deficits and degeneration in the rat optic nerve", *Invest Ophthalmol Vis Sci* 33(13): 3586-3591 (1992)

Yoles et al, "Degeneration of spared axons following partial white matter lesion: implications for optic nerve neuropathies", *Exp. Neurol.* 153: 1-7 (1998a)

Yoles et al, "Elevation of intraocular glutamate levels in rats with partial lesion of the optic nerve", *Arch Ophthalmol,* 116: 906-910 (1998)

Yoles et al, *J Neurosci* (2000)

Yoshino et al, "Dynamic changes in local cerebral glucose utilization following cerebral conclusion in rats: evidence of a hyper- and subsequent hypometabolic state", *Brain Res* 561(1): 106-119 (1991)

Zaroulis et al, "Successful freeze-preservation of human granulocytes", *Cryobiology* 17(3): 311-317 (1980)

Zivin et al, "Stroke therapy", *Sci Am* 265(1): 56-63 (1991)

What is claimed is:

1. A method for reducing secondary neuronal degeneration that follows neuronal damage caused by glaucoma in an individual in need thereof, comprising:

causing T cells activated by Copolymer 1 or a Copolymer 1-related peptide or polypeptide that is a random copolymer that cross-reacts functionally with myelin basic protein (MBP) and is capable of competing with MBP on the MHC class II molecule in antigen presentation, to accumulate at the site of neuronal degeneration in the individual in need, thereby reducing neuronal degeneration at that site, wherein said causing step comprises—administering an effective amount of said Copolymer 1 or said Copolymer 1-related peptide or polypeptide in such a manner as to cause a T cell response thereto, such that T cells become activated by said Copolymer 1 or Copolymer 1 related peptide or polypeptide; or administering an effective amount of activated T cells that have been activated by said Copolymer 1 or said Copolymer 1-related peptide or polypeptide.

2. A method in accordance with claim 1, wherein said Copolymer 1 or Copolymer 1-related peptide or polypeptide is Copolymer 1.

3. A method in accordance with claim 1, wherein said random copolymer comprises one amino acid residue selected from each of at least three of the following groups:

(a) lysine and arginine;
(b) glutamic acid and aspartic acid;
(c) alanine and glycine; and
(d) tyrosine and tryptophan.

4. A method in accordance with claim 3, wherein said random copolymer consists of four different amino acid residues, each from a different one of the groups (a) to (d).

5. A method in accordance with claim 4, wherein said four different amino acid residues are alanine, glutamic acid, lysine and tyrosine.

6. A method in accordance with claim 3, wherein said random copolymer consists of three different amino acid residues, each from a different one of three groups (a) to (d).

7. A method in accordance with claim 6, wherein said three different amino acid residues are tyrosine, alanine, and lysine.

8. A method in accordance with claim 6, wherein said three different amino acid residues are tyrosine, glutamic acid and lysine.

9. A method in accordance with claim 6, wherein said three different amino acid residues are lysine, glutamic acid, and alanine.

10. A method in accordance with claim 6, wherein said three different amino acid residues are tyrosine, glutamic acid, and alanine.

11. A method in accordance with claim 1, wherein said activated T cells are caused to accumulate at the site of secondary neuronal degeneration by administering an effective amount of said Copolymer 1 or said Copolymer 1-related peptide or polypeptide in such a manner as to cause a T cell response thereto, such that T cells become activated by said Copolymer 1 or said Copolymer 1-related peptide or polypeptide.

12. A method in accordance with claim 11, wherein said Copolymer 1 or Copolymer 1-related peptide or polypeptide is Copolymer 1.

13. A method in accordance with claim 11, wherein said Copolymer 1 or Copolymer 1-related peptide or polypeptide is said Copolymer 1-related peptide or polypeptide.

14. A method in accordance with claim 11, in which said Copolymer 1 or Copolymer 1-related peptide or polypeptide is administered in a manner which promotes active immunization of the individual so as to build up a critical T cell response.

15. A method in accordance with claim 11, wherein said random copolymer comprises one amino acid residue selected from each of at least three of the following groups:
(a) lysine and arginine; (b) glutamic acid and aspartic acid; (c) alanine and glycine; and (d) tyrosine and tryptophan.

16. A method in accordance with claim 15, wherein said random copolymer consists of four different amino acid residues, each from a different one of the groups (a) to (d).

17. A method in accordance with claim 16, wherein said four different amino acid residues are alanine, glutamic acid, lysine and tyrosine.

18. A method in accordance with claim 15, wherein said random copolymer consists of three different amino acid residues, each from a different one of three groups (a) to (d).

19. A method in accordance with claim 18, wherein said three different amino acid residues are tyrosine, alanine, and lysine.

20. A method in accordance with claim 18, wherein said three different amino acid residues are tyrosine, glutamic acid and lysine.

21. A method in accordance with claim 18, wherein said three different amino acid residues are lysine, glutamic acid, and alanine.

22. A method in accordance with claim 18, wherein said three different amino acid residues are tyrosine, glutamic acid, and alanine.

23. A method in accordance with claim 1, wherein said activated T cells are caused to accumulate at the site of secondary neuronal degeneration by administering an effective amount of activated T cells that have been activated by said Copolymer 1 or said Copolymer 1 related peptide or polypeptide.

24. A method in accordance with claim 23, wherein said activated T cells are autologous T cells, or allogeneic T cells from related donors, or HLA-matched or partially matched, semi-allogeneic or fully allogeneic donors.

25. A method in accordance with claim 24, wherein said T cells are autologous T cells which have been stored or are derived from autologous central nervous system (ONS) cells.

26. A method in accordance with claim 24, wherein said T cells are semi-allogeneic T cells.

27. A method for ameliorating the secondary neurodegenerative effects of glaucoma in an individual in need thereof, comprising:
causing T cells activated by Copolymer 1 or a Copolymer 1-related peptide or polypeptide that is a random copolymer that cross-reacts functionally with myelin basic protein (MBP) and is capable of competing with MBP on the MHC class II molecule in antigen presentation, to accumulate at the site of secondary neuronal degeneration in the individual in need, thereby reducing secondary neuronal degeneration at that site, wherein said causing step comprises—administering an effective amount of said Copolymer 1 or said Copolymer 1-related peptide or polypeptide in such a manner as to cause a T cell response thereto, such that T cells become activated by said Copolymer 1 or Copolymer 1-related peptide or polypeptide; or administering an effective amount of activated T cells that have been activated by said Copolymer 1 or said Copolymer 1-related peptide or polypeptide.

* * * * *